United States Patent
Shen et al.

(10) Patent No.: US 12,315,626 B2
(45) Date of Patent: May 27, 2025

(54) AUTOMATED PROTOCOLING IN MEDICAL IMAGING SYSTEMS

(71) Applicant: GE Precision Healthcare LLC, Wauwatosa, WI (US)

(72) Inventors: Yaxi Shen, Waukesha, WI (US); Vignesh Doraiswamy, New Berlin, WI (US); Amanda Ciano, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 255 days.

(21) Appl. No.: 17/777,477

(22) PCT Filed: Nov. 24, 2020

(86) PCT No.: PCT/US2020/061999
§ 371 (c)(1),
(2) Date: May 17, 2022

(87) PCT Pub. No.: WO2021/108398
PCT Pub. Date: Jun. 3, 2021

(65) Prior Publication Data
US 2022/0399107 A1 Dec. 15, 2022

Related U.S. Application Data

(60) Provisional application No. 62/941,995, filed on Nov. 29, 2019.

(51) Int. Cl.
*G16H 40/40* (2018.01)
*G16H 30/20* (2018.01)

(52) U.S. Cl.
CPC .............. *G16H 40/40* (2018.01); *G16H 30/20* (2018.01)

(58) Field of Classification Search
None
See application file for complete search history.

(56) References Cited

U.S. PATENT DOCUMENTS

2005/0121505 A1 6/2005 Metz
2013/0090946 A1* 4/2013 Foo .................. G16H 10/65
705/3

(Continued)

OTHER PUBLICATIONS

Taha et al. ("Metrics for evaluating 3D medical image segmentation: analysis, selection, and tool." BMC Med Imaging 15, 29 (2015) ) (Year: 2015).*

(Continued)

*Primary Examiner* — Christopher B Tokarczyk

(57) ABSTRACT

The present disclosure relates to leveraging machine learning algorithms to help guide users to effortlessly assign the correct protocol for an exam order using a standard protocol library and patient clinical information, and it further automates the scanner protocol selection creating a seamless workflow. This helps to reduce time for protocoling and ensures the right imaging exam is delivered for the patient in an efficient manner. In accordance with certain embodiments, a method includes receiving an order for a medical imaging procedure. The medical imaging procedure corresponds to a patient, in response to receding receiving the order, obtaining medical information stored in an information technology system. The medical information relates to the patient, and automatically generating a medical imaging protocol as a function of the obtained medical information.

19 Claims, 12 Drawing Sheets

(56) References Cited

U.S. PATENT DOCUMENTS

2013/0311472 A1\* 11/2013 Cohen-Solal .......... G16H 30/20
                                                707/737
2015/0085971 A1    3/2015 Braun
2018/0144822 A1\* 5/2018 Guendel ................ G06N 20/20
2018/0330818 A1   11/2018 Hsieh
2019/0131011 A1\* 5/2019 Sevenster ............. G16H 30/20

OTHER PUBLICATIONS

International Application No. PCT/US2020/061999 filed Nov. 24, 2020—International Search Report and Written Opinion issued on Mar. 25, 2021; 23 pages.
EP application 20893134.5 filed May 20, 2022—extended Search Report issued FEb. 8, 2024; 17 pages.

\* cited by examiner

AUTOMATED PROTOCOLING IN MEDICAL IMAGING SYSTEMS

CROSS-REFERENCE TO RELATED APPLICATION

This application claims the benefit of and priority to U.S. Provisional Application No. 62/941,995, filed on Nov. 29, 2019, and claims priority to PCT Application No. PCT/US2020/061999, filed on Nov. 24, 2020, the disclosures of which are incorporated herein by reference in their entirety.

TECHNICAL FIELD

This disclosure relates to medical imaging protocols and more particularly to systems and methods for automating the selection of medical imaging protocols.

BACKGROUND

In order to visualize an internal structure (i.e., organ, tissue, bone, etc.) a physician may order a patient undergo a medical imaging procedure. The physician's orders may include a generic description of an imaging procedure (hereinafter referred to as a "physician order") and are sent to a radiologist. A radiologist reads the physician order and reviews the patient's medical history to recommend a radiologist level protocol per the physician order. For example, when the physician's orders include a "computed tomography (CT) scan of the abdomen for flank pain" the radiologist may review the patient's medical history and determine the patient has previously undergone a contrast CT scan of the abdomen and may determine it is appropriate to perform a similar scan. Accordingly, the radiologist will map "CT scan of the abdomen with contrast" to the physician order in an information technology (IT) system, typically the radiology information system (RIS). The radiologist's orders (hereinafter referred to as a "radiologist level protocol") are then converted into technical instructions and sent to a technologist who operates the scanner. The technologist uses the protocolled order and selects the specific technical settings (hereinafter referred to as a "scanner level protocol") on a given imaging device based on the radiologist level protocol. Some imaging devices include a user interface (UI) that provides a list of scanner level protocols to the technologist. In this instance, the technologist determines and selects the most appropriate scanner level protocol based on the radiologist level protocol. This process (from physician ordering a medical imaging procedure to a technologist determining and/or selecting the most appropriate scanner level protocol for an imaging device) may be generally referred to as the "medical imaging protocoling process." After the medical imaging protocoling process is complete, the medical imaging procedure may begin.

SUMMARY

In one embodiment, the present disclosure provides a method. The method includes receiving an order for an imaging procedure. The imaging procedure corresponds to a patient. In response to receiving the order, obtaining medical information stored in an information technology system. The medical information relates to the patient. And automatically generating an imaging protocol as a function of the received order and the obtained medical information.

In another embodiment, the present disclosure provides another method. The method includes receiving a plurality of scan protocols and a plurality of patient-specific medical information from one or more storage devices. Extracting a plurality of first domain concepts from the plurality of scan protocols and a plurality of second domain concepts from the plurality of patient-specific medical information. In response to matching a subset of the plurality of scan protocols to the plurality of patient-specific medical data based on the plurality of first domain concepts and the plurality of second domain concepts, selecting one of the subsets of scan protocols.

In yet another embodiment, the present disclosure provides a computer readable storage medium with computer readable program instructions that, when executed by a processor, cause the processor to: receive a plurality of scan protocols and a plurality of patient-specific medical information from one or more storage devices; extract a plurality of first domain concepts from the plurality of scan protocols and a plurality of second domain concepts from the plurality of patient-specific medical information; in response to matching a subset of the plurality of scan protocols to the plurality of patient-specific medical data based on the plurality of first domain concepts and the plurality of second domain concepts; and select one of the subsets of scan protocols.

BRIEF DESCRIPTION OF THE DRAWINGS

Various aspects of this disclosure may be better understood upon reading the following detailed description with reference to the drawings in which.

Figure 1:
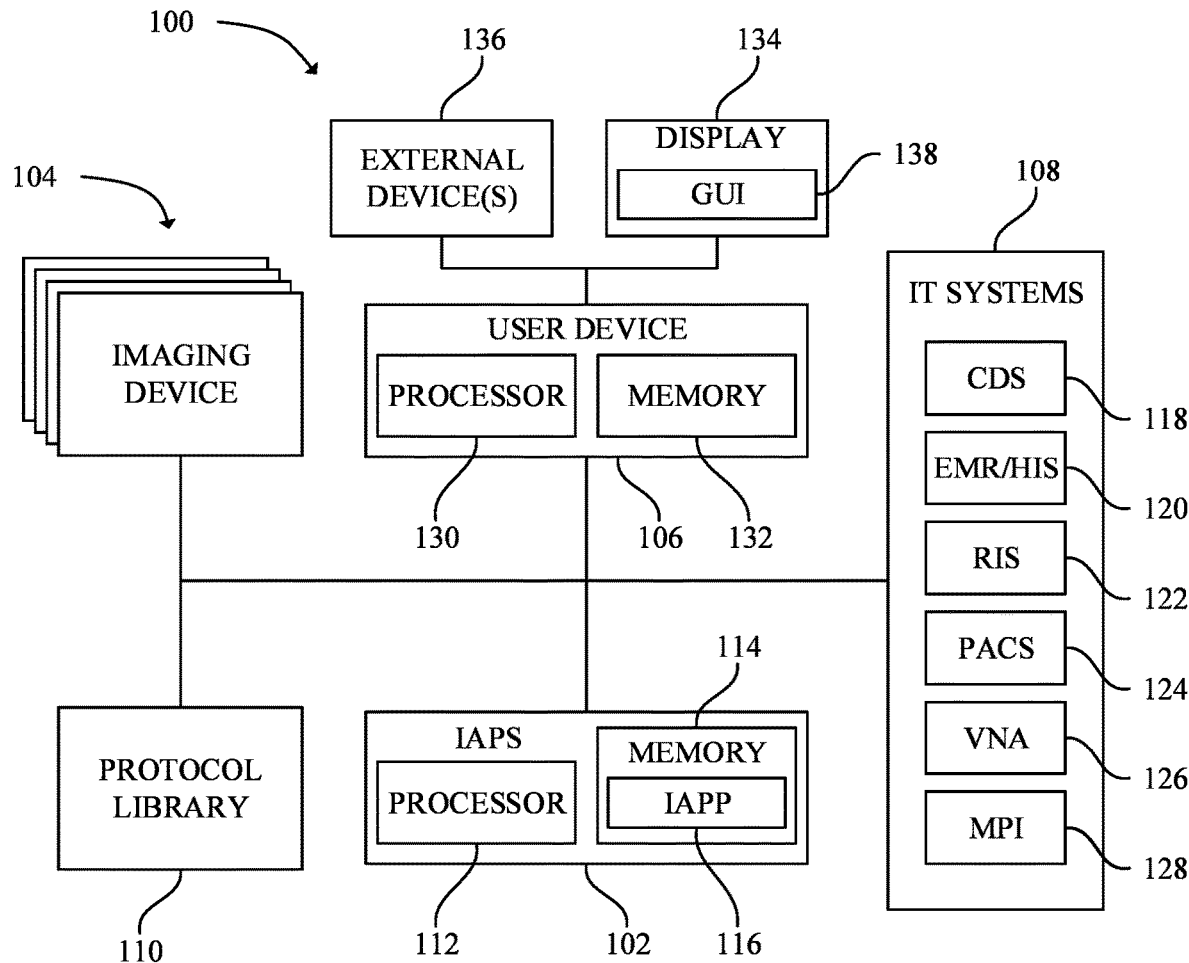
FIG. 1 is a block diagram of a medical imaging system in accordance with an exemplary embodiment.

The drawings illustrate specific acts of the described components, systems, and methods for automating the selection of medical imaging protocols. Together with the following description, the drawings demonstrate and explain the structures, methods, and principles described herein. In the drawings, the thickness and size of components may be exaggerated or otherwise modified for clarity. Well-known structures, materials, or operations are not shown or described in detail to avoid obscuring aspects of the described components, systems, and methods.

DETAILED DESCRIPTION

One or more specific embodiments of the present disclosure are described below. These described embodiments are only examples of the systems and methods for automating the selection of medical imaging protocols. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

The protocoling process includes a physician ordering a medical imaging procedure after examining a patient. Different medical professionals may have different training or experiences which influence their decision on what and/or how an anatomy should be imaged. Furthermore, any given patient may have a significant medical history which may preclude agreement between any two medical professionals due to a vast number of decision points. For example, two medical professionals may consider clinical indications, medical history, prior exam images, and other prior reports for a patient; each step of the diagnosis process presents an opportunity for a divergence in medical imaging procedure recommendation. A physician order includes a generic description of a medical imaging procedure including a device/system that will perform the imaging and an anatomy to be imaged (i.e., a CT scan of the abdomen).

The protocoling process further includes sending the physician order to a radiologist so that the radiologist may generate a radiologist level protocol based on the physician order. To generate the radiologist level protocol, the radiologist may review medical information pertaining to the patient to be imaged from various IT systems. A radiologist level protocol may include information regarding a medical imaging procedure including, but not limited to, contrast agents used, direction of imaging, type of imaging procedure, and clinical instructions of a technologist to perform a medical imaging procedure. Some embodiments of the present disclosure provide a system and/or method that reviews medical information (i.e., age, gender, height, weight, demographic information, medical images, medical history, diagnoses, medications, allegories, lab results, physician orders, medical codes etc.) and automatically generates a radiologist level protocol as a function of the medical information. These systems/methods provide radiologist level protocol that is personalized to the patient as it is based on the patient's medical information and saves the radiologist time as the radiologist does not need to search through the patient medical information to generate the radiologist level protocol.

The protocolling process also includes sending the radiologist level protocol to a technologist so that the technologist may generate a scanner level protocol based on the radiologist level protocol. A scanner level protocol includes technical imaging parameters specific to a medical imaging device including, but not limited to, kV mA, contrast, timing, scan speed, and anatomic coverage. If the technologist then has questions, the radiologist may be consulted for further review. In some examples, a given radiologist may have a high caseload or a given medical facility may be insufficiently staffed (i.e., may not employ an in-house radiologist), and a larger portion of protocol generation may be performed by less-experienced individuals. Further, experience may not only vary by individual or profession, but also by medical facility, such that there may exist geographic variability in scanning proficiency and consistency. Some embodiments of the present disclosure provide systems/methods that automatically selects a scanner level protocol based on the radiologist level protocol. Providing a system/method that automatically selects a scanner level protocol based on a radiologist level protocol may save the technologist and radiologist time as the technologist may not question the radiologist for a scanner level protocol.

Referring to the figures generally, the present disclosure describes systems and methods for automating the medical imaging protocol process.

Referring now to FIG. 1, a block diagram of a medical imaging system 100 is shown in accordance with an exemplary embodiment. As illustrated in FIG. 1, in some embodiments, the medical imaging system 100 includes an intelligent automated protocoling system (TAPS) 102, a plurality of medical imaging devices 104, a user device 106, information technology (IT) systems 108, and a global protocol library 110.

The IAPS 102 is a computing device. As used herein, a computing device (or system) is any device/system capable of processing and transmitting data (i.e., tablet, handheld computing device, smart phone, personal computer, laptop, network computer, server, mobile communication device, server, etc.). In one embodiment, the IAPS 102 may take the form of an edge device for interfacing between the medical imaging devices 104, the user device 106, the IT systems 108, and the protocol library 110. In another embodiment, the IAPS 102 may be located in a room of a medical facility (i.e., clinic, hospital etc.) that is remote form the imaging devices 104. In yet another embodiment, the IAPS 102 may take the form of a server of a cloud computing environment. While FIG. 1 depicts the IAPS 102 as separate from the imaging devices 104, in yet another embodiment, one or more imaging devices 104 may include the IAPS 102. The imaging devices 104, the user device 106, the IT systems 108, and the global protocol library 110 are connected to the IAPS 102 via a wired or wireless connection thereby allowing the IAPS 102 to transmit data to/receive data from the imaging devices 104, the user device 106, the IT systems 108, and the global protocol library 110. In one embodiment, the IAPS 102, the imaging devices 104, the user device 106, the IT systems 108, and the global protocol library 110 may be connected to a network (i.e., a wide area network (WAN), a local area network (LAN), a public network (the Internet), etc.) which allows the IAPS 102, the imaging devices 104, the user device 106, the IT systems 108, and the global protocol library 110 to communicate with one another when connected to a same network. In some embodiments, the network may be regarded as a private network connection and may include, for example, a virtual private network or an encryption or other security mechanism employed over the public Internet.

The IAPS 102 includes a processor 112 and a system memory 114. The processor 112 is in communication with the system memory 114 and may execute computer readable program instructions stored in the system memory 114. In one embodiment, a processor may include a central processing unit (CPU). In another embodiment, a processor may include other electronic components capable of executing computer readable program instructions, such as a digital signal processor, a field-programmable gate array (FPGA), or a graphics board. In yet another embodiment, a processor may be configured as a graphical processing unit with parallel processing capabilities. In yet another embodiment, a processor may include multiple electronic components capable of carrying out computer readable instructions. For example, a processor may include two or more electronic components selected from a list of electronic components including: a CPU, a digital signal processor, an FPGA, and a graphics board.

The system memory 114 is a computer readable storage medium. As used herein a computer readable storage medium is any device that stores computer readable program instructions for execution by a processor and is not construed as being transitory per se. Computer readable program instructions include programs, logic, data structures, modules, architecture etc. that when executed by a processor create a means for implementing functions/acts. Computer readable program instructions when stored in a computer readable storage medium and executed by a processor direct a computer system and/or another device to function in a particular manner such that a computer readable storage medium comprises an article of manufacture. System memory as used herein includes volatile memory (i.e., random access memory (RAM) and dynamic RAM (DRAM)) and nonvolatile memory (i.e., flash memory, read-only memory (ROM), magnetic computer storage devices, etc.). In some embodiments, the system memory may further include cache. The system memory 114 stores an intelligent automated protocoling program (IAPP) 116 in the form of computer readable program instructions. As will be discussed in further detail herein, when executed, the IAPP 116 causes the IAPS 102 to generate a radiologist level protocol as a function of received medical information, select one or more scanner level protocols as a function of a radiologist level protocol and output the radiologist level protocol and/or the selected scanner level protocol(s) to a display.

The IAPS 102 and the medical imaging devices 104 may be communicably coupled to one another. In some embodiments, each of the medical imaging devices 104 may correspond to a different imaging modality (i.e., X-ray, magnetic resonance imaging (MRI), ultrasound (US), CT, positron emission tomography (PET), single-photon emission CT (SPECT), and combinations thereof (i.e., multi-modality imaging, such as PET/CT, PET/MR, SPECT/CT, etc.). In other embodiments, each of the medical imaging devices 104 may correspond to the same imaging modality, whereby each of the medical imaging devices 104 may be located in a separate room (i.e., in a hospital) or in separate facilities (i.e., hospitals) altogether. In still other embodiments not depicted at FIG. 1, the medical imaging system 100 may include only one medical imaging device 104 directed to a single imaging modality (i.e., such as in the CT imaging system as described below with reference to FIGS. 2 and 3).

The IAPS 102 is in further communication with the global protocol library 110. The global protocol library 110 is a database of medical imaging protocols including physician level, radiologist level, and scanner level protocols. The global protocol library 110 may be stored in a computer readable storage medium and may be accessed by the IAPS 102. Furthermore, the imaging devices 104 and the user device 106 may be in communication with the global protocol library 110, such that the imaging devices 104 and/or the user device 106 may update the global protocol library 110 by adding, removing, substituting, or otherwise altering medical imaging protocols stored in the global protocol library 110

The IAPS 102 is in communication with the IT systems 108. The IT systems 108 include one or more clinical decision support systems (CDS) 118, electronic health or medical records and/or hospital information systems (EMR/HIS) 120, radiological information systems (RIS) 122, picture archiving and communications systems (PACS) 124, vendor neutral archives (VNA) 126, master patient indices (MPI) 128. The IAPS 102 may access the IT systems 108 and obtain medical information relating to a patient. As an example, the PACS 124 stores medical images generated by the medical imaging devices 104 or other medical imaging devices that are not included in the medical imaging devices 104. As another example, the EMR/HIS 120 stores medical information (i.e., clinical indications, patient medical histories, patient allergies, etc.). As yet another example, the RIS 122 stores medical information relating to radiology (i.e., prior reports, modality worklists, prior exam images, etc.).

The IAPS 102 is in communication with the user device 106. The user device 106 may be a computing device and includes a processor 130 and a system memory 132. The user device 106 is further connected to a display 134 and one or more external devices 136. The one or more external devices 136 includes devices that allow a user to interact with/operate the user device 106. The display 134 displays a graphical user interface (GUI) 138. The GUI 138 includes editable fields for inputting data including, but not limited to, patient information and further includes selectable icons. Selecting an icon or inputting data causes the processor 130 or the processor 112 to execute computer readable program instructions stored in the system memory 132 or the system memory 114 to perform a task. A user of the user device 106 may use an external device 136 to select an icon and/or input patient information. Inputting patient information and/or selecting an icon may cause the processor 130 of the user device 106 to query the IAPS 102 for a medical imaging protocol (i.e., physician order, a radiologist level protocol, or a scanner level protocol). In some embodiments, the user device 106 is in further communication with the imaging devices imaging devices 104. In these embodiments, a user of the user device 106 may use an external device 136 to select a "start" icon or the like which causes the processor 130 to control a medical imaging device 104 to begin an imaging procedure.

Figure 2:
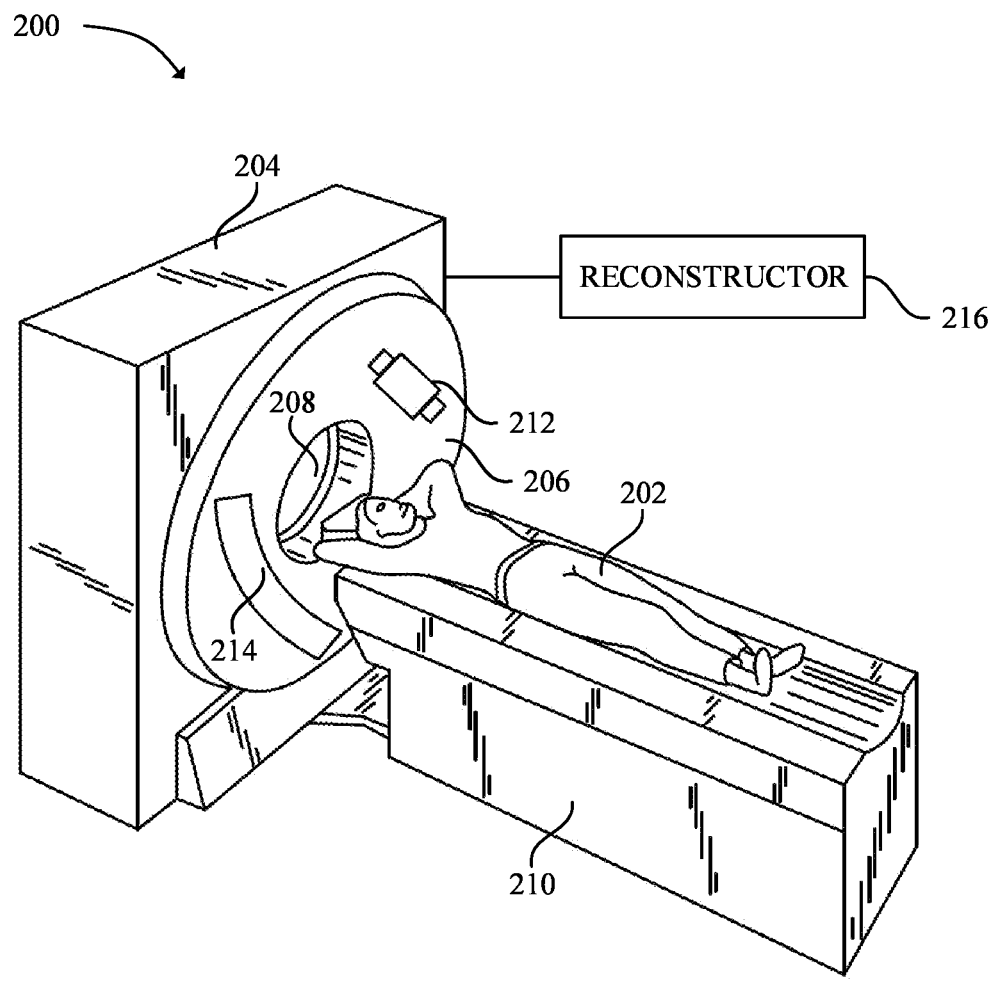
FIG. 2 depicts a CT system in accordance with an exemplary embodiment.
Figure 3:
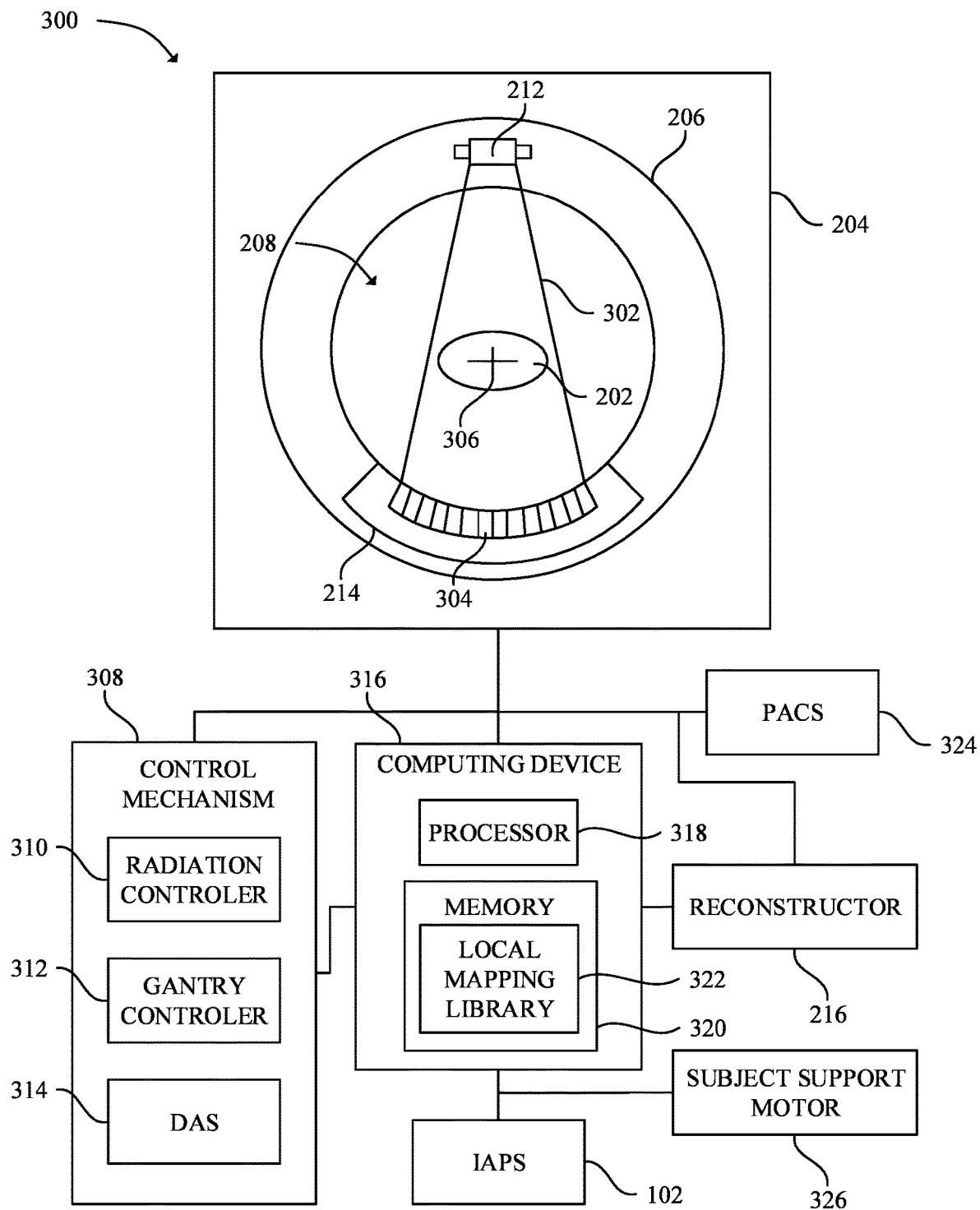
FIG. 3 is a block diagram of a CT system in accordance with an exemplary embodiment.

In some embodiments, the IAPS 102 may be configured to interface with the imaging devices 104, such that the IAPS 102 may be configured to select an imaging device 104 corresponding to an appropriate imaging modality for a given scanner level protocol. However, in other embodiments, the IAPS 102 may be configured to interface with one or more imaging devices 104 corresponding to only one imaging modality. That is, in some embodiments, the medical imaging system 100 may be directed to a specific imaging modality. Accordingly, FIGS. 2 and 3 provide an exemplary CT imaging system wherein the IAPS 102 is directed to a single imaging modality.

In operation, the IAPS 102 and/or the user device 106 may acquire medical data (i.e., from the IT systems 108) and imaging data (i.e., from the medical imaging devices 104), which may be translated for display to a user on the display 134. As an example, the medical data may be transformed into and displayed at the display 134 as a user-facing graphical and/or textual format, which may be standardized across multiple user devices 106 or may be particular to a given facility, department, profession, or individual user. As another example, the imaging data (i.e., three-dimensional (3D) volumetric data sets, two-dimensional (2D) imaging slices, etc.) may be used to generate one or more images at the IAPS 102 or the user device 106, which may then be displayed to the user or user at the display 134.

The IAPS 102 or the user device 106 may implement an image-processing module which may process the imaging data. For example, the image-processing module may process 3D volumetric imaging data to generate 2D image slices for displaying to the user of the medical imaging system 100. Similarly, the image processing module may process the imaging data to generate 3D renderings for displaying to the user. It will be appreciated that acquired imaging data may be processed in real-time during an imaging session as signals are received at the given imaging device 104. Additionally, or alternatively, the imaging data may be stored temporarily in a system during the medical imaging procedure and processed in less than real-time in a live or off-line operation.

In addition to the image-processing module, the IAPS 102 or the user device 106 may also implement one or more of a graphics module, an initialization module, a tracking module, and an analysis module. The image-processing module, the graphics module, the initialization module, the tracking module, and the analysis module may coordinate to present information to the user during and after an imaging session. For example, the image-processing module, when executed, may cause the processor 112 or the processor 130 to output an acquired image on the display 134, and the graphics module, when executed, may cause the processor 112 or the processor 130 to output designated graphics (i.e., selectable icons and measurement parameters relating to an image) along with an image to the display 134.

A screen area of the display 134 may be made up of a series, or matrix, of pixels which display the imaging data acquired with the imaging devices 104. The acquired imaging data may include one or more imaging parameters calculated for each pixel, or group of pixels (for example, a group of pixels assigned the same parameter value), of the display 134, where the one or more calculated image parameters may include one or more of an intensity, velocity (i.e., blood flow velocity), color flow velocity, texture, graininess, contractility, deformation, and rate of deformation value. The series of pixels may then make up the displayed image generated from the acquired imaging data.

In some embodiments, IAPS 102 may implement a deep learning module which includes one or more deep neural networks (i.e., a system of neural networks, as described in detail below with reference to FIGS. 4 and 5) and instructions for performing deep learning functionalities described herein. For example, the intelligent IAPS 102 may implement the deep learning module such that the IAPS 102 may adaptively "learn" and recognize patterns in a series of executed medical imaging protocols stored in the global protocol library 110 and medical information stored IT systems 108 to generate and/or select one or more medical imaging protocols for a given patient. As such, the IAPS 102 may be configured to periodically update the deep learning module such that protocol generation and/or protocol selection may be made more consistent over time (in that medical expertise is accumulated over continued use of the medical imaging system 100), thereby incrementally improving patient experience and health outcomes. As such, it will be appreciated that the IAPS 102 and the IT systems 108 may update information related to medical imaging procedures in an asynchronous manner, allowing the IAPS 102 to analyze and generate different, but related, data structures to those stored on the IT systems 108.

Referring now to FIG. 2 a CT system 200 is shown in accordance with an exemplary embodiment. The CT system 200 is configured to image a patient 202. In one embodiment, the CT system 200 includes a generally stationary gantry 204, a and a rotating gantry 206 which is supported by the stationary gantry 204 and rotates around an examination region 208. A subject support 210 such as a couch, bed, table, etc. supports the patient 202 while the patient 202 is in the examination region 208.

The CT system 200 further includes an X-ray radiation source 212 such as an X-ray tube that is supported by the rotating gantry 206, rotates with the gantry 206, and emits radiation that traverses the examination region 208. In one embodiment, the X-ray radiation source 212 includes a single broad-spectrum X-ray tube. In another embodiment, the X-ray radiation source 212 incudes a single X-ray tube configured to switch between at least two different emission voltages (i.e., 80 kVp and 140 kVp) during an imaging session. In yet another embodiment, the X-ray radiation source 212 includes two or more X-ray tubes configured to emit radiation having different mean spectra. In yet another embodiment, the X-ray radiation source 212 includes a combination thereof.

The CT system 200 further includes a radiation sensitive detector array 214. The radiation sensitive detector array 214 includes a one- or two-dimensional array of rows of detector elements (not shown in FIG. 2) and subtends an angular arc opposite the X-ray radiation source 212 across the examination region 208. The radiation sensitive detector array 214 detects radiation traversing the examination region 208 that is attenuated by the patient 202 and generates projection data. The intensity of the detected radiation is dependent upon the attenuation by the patient 202. Each detector element of the radiation sensitive detector array 214 produces a separate electrical signal that is a measurement of the attenuation at the detector location. The attenuation measurements from all the detector elements are acquired separately to produce a transmission profile. In some embodiments, the radiation sensitive detector array 214 is a photon-counting detector which is capable of differentiating X-ray photons of different energies. In other embodiments, the radiation sensitive detector array 214 includes detector elements that are used to generate dual-energy projections, with one set at low-kVp and the other at high-kVp. It should thus be appreciated that the methods described herein may be implemented with single energy acquisition techniques as well as dual energy acquisition techniques.

The projection data undergoes pre-processing and calibration to condition the data to represent the line integrals of the attenuation coefficients of the patient 202. The processed data are commonly called projections. The acquired sets of projection data may be used for basis material decomposition (BMD). During BMD, the measured projections are converted to a set of density line-integral projections.

The X-ray radiation source 212 and the radiation sensitive detector array 214 are rotated the rotating gantry 206 about the examination region 208 and the patient 202 such that an angle at which radiation emitted by the X-ray radiation source 212 intersects the patient 202 constantly changes. A group of X-ray radiation attenuation measurements (projection data) from the radiation sensitive detector array 214 at one angular position of the rotating gantry 206 is referred to as a "view." A "scan" of the object includes a set of views made at different angular positions, or view angles, during one revolution of the X-ray radiation source 212 and radiation sensitive detector array 214 about the patient 202. It is contemplated that the benefits of the methods described herein accrue to medical imaging modalities other than CT, so as used herein the term "view" is not limited to the use as described above with respect to projection data from one rotating gantry 206 angle. The term "view" is used to mean one data acquisition whenever there are multiple data acquisitions from different angles, whether from a CT, X-ray radiographic imaging, positron emission tomography (PET), or single-photon emission CT (SPECT) acquisition, and/or any other modalities as well as combinations thereof.

To reduce a total scan time, a "helical" scan may be performed. To perform a "helical" scan, the patient is moved while the data for the prescribed axial coverage is acquired. Such a system generates a single helix from a cone-beam helical scan. The helix yields projection data from which images in each prescribed slice may be reconstructed.

The CT system 200 further includes a reconstructor 216. The reconstructor 216 may be implemented by the IAPS 102, the user device 106, or another computing device. The reconstructor 216 receives the projection data and processes the projection data to reconstruct an image that corresponds to one or more two-dimensional slices taken through the patient 202 or, in some examples where the projection data includes extended axial coverage, i.e., Z-axis illumination, a three-dimensional image volume of the object. The reconstructor 216 reconstructs an image using an iterative or analytic image reconstruction method, or a combination of both. For example, the reconstructor 216 may use an analytic image reconstruction approach such as filtered back projection (FBP) to reconstruct images of a target volume of the patient 202. As another example, the reconstructor 216 may use an iterative image reconstruction approach such as advanced statistical iterative reconstruction (ASIR) or model-based iterative reconstruction (MBIR), and the like, to reconstruct images of a target volume of the patient 202. In some examples, the reconstructor 216 may use both an analytic image reconstruction approach such as FBP in addition to an iterative image reconstruction approach. Transmission and emission tomography reconstruction techniques also include statistical iterative methods such as maximum likelihood expectation maximization (MLEM) and ordered-subsets expectation maximization reconstruction techniques as well as iterative reconstruction techniques. This process converts the attenuation measurements from a scan into integers called "CT numbers" or "Hounsfield units," which are used to control the brightness of a corresponding pixel on a display device.

In one embodiment, the reconstructor 216 reconstructs density line-integral projections to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume. Once reconstructed, a basis material image produced by the system 200 reveals internal features of the patient 202, expressed in the densities of two basis materials. The density image, or combinations of multiple density images, may be displayed to show these features. In traditional approaches to diagnosis of medical conditions, such as disease states, and more generally of medical events, a radiologist or physician would consider a hard copy or display of the density image, or combinations thereof, to discern characteristic features of interest. Such features might include lesions, sizes and shapes of particular anatomies or organs, and other features that would be discernable in the image based upon the skill and knowledge of the individual practitioner.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Referring now to FIG. 3, another CT system 300 is shown in accordance with an exemplary embodiment. The CT system 300 is configured to image the patient 202. In one embodiment, the CT system 300 includes an enclosure and frame assembly 204 that supports a rotating gantry 206. In certain embodiments, the rotating gantry 206 rotates around the examination region 208. In these embodiments, the rotating gantry 206 may be configured to rotate about a center of rotation 306 for acquiring projection data, for example, at different energy levels. The rotating gantry 206 supports an X-ray radiation source 212 and the radiation sensitive detector array 214. The X-ray radiation source 212 emits X-ray radiation 302 that traverses the examination region 208 and is attenuated by the patient 202. The radiation sensitive detector array 214 includes a plurality detector elements 304. The detector elements 304 detect the attenuated X-ray radiation that passes through the patient 202 to acquire corresponding projection data. Accordingly, in one embodiment, the radiation sensitive detector array 214 is fabricated in a multi-slice configuration including the plurality of rows of cells or detector elements 304. In such a configuration, one or more additional rows of the detector elements 304 are arranged in a parallel configuration for acquiring the projection data.

In one embodiment, the system 300 includes a control mechanism 308 that controls movement of the components of the CT system 300 such as rotation of rotating gantry 206 and the operation of the X-ray radiation source 212. The control mechanism 308 includes radiation controller 310 configured to provide power and timing signals to the X-ray radiation source 212. The control mechanism 308 further includes a gantry motor controller 312 configured to control a rotational speed and/or position of the rotating gantry 206 based on imaging requirements.

In certain embodiments, the control mechanism 308 further includes a data acquisition system (DAS) 314 that samples analog data received from the detector elements 304 and converts the analog data to digital signals for subsequent processing. For photon-counting imaging systems, the DAS 314 downloads measured photon counts in one or more energy bins from detector array 214. The data sampled and digitized by the DAS 314 is transmitted to a computing device 316. In some embodiments, the computing device is the user device 106.

The computing device 316 includes a processor 318 and a system memory 320. The system memory 320 stores the received data from the DAS 314 and includes a local mapping library 322. The local mapping library 322 stores previous scanner level protocol selections for a given medical imaging device, in this instance the CT system 300. Each medical imaging device 104 may be in communication with a similar local mapping library as depicted in FIG. 3. While the local mapping library 322 is depicted as store in the system memory 320, it is understood that the local mapping library 322 may be stored in any computer readable storage medium disclosed herein.

Additionally, the computing device 316 provides commands and parameters to one or more of the DAS 314, the radiation controller 310, and the gantry motor controller 312 for controlling system operations such as data acquisition and/or processing. In certain embodiments, the computing device 316 controls system operations based on user input. For example, the computing device 316 may receive the user input including commands and/or scanning parameters via a keyboard (not shown) or a touchscreen to allow the user to specify the commands and/or scanning parameters.

Although FIG. 3 illustrates only one computing device 316, more than one computing device 316 may be coupled to the DAS 314, for example, for inputting or outputting system parameters, requesting examinations, plotting data, and/or viewing images. Further, in certain embodiments, the system 300 may be coupled to multiple displays, printers, workstations, and/or similar devices located either locally or remotely, for example, within an institution or hospital, or in an entirely different location via one or more configurable wired and/or wireless networks. In one embodiment, the computing device 316 is in communication with a PACS 324. In some embodiments, the PACS 324 is the PACS 124. The PACS 324 is in communication with to a remote system such as an RIS, EMR/HIS, and/or to an internal or external network (not shown) to allow users at different locations to supply commands and parameters and/or gain access to the image data stored therein.

The computing device 316 is further connected to and is in communication with a subject support control motor 326. A user of the computer device 316 may use the computer device 316 to supply commands and parameters to operate the subject support control motor 326, which in turn, may control the subject support 210. Specifically, the subject support control motor 326 may move the subject support 210 for appropriately positioning the patient 202 in the examination region 208 for acquiring projection data corresponding to a target volume of the patient 202.

The DAS 314 is further connected to and in communication with the reconstructor 216. The DAS 314 sends the sampled and digitized projection data to the reconstructor 216. The reconstructor 216 uses the sampled and digitized X-ray data to perform high-speed reconstruction. In some embodiments the computing device 316 may include the reconstructor 216. Alternatively, the reconstructor 216 may be absent from the system 300 and instead the computing device 316 may perform one or more functions of the reconstructor 216. Moreover, the reconstructor 216 may be located locally or remotely, and may be operatively connected to the system 300 using a wired or wireless network. For example, one embodiment may use computing resources in a cloud network cluster for the reconstructor 216.

The image reconstructor 216 stores reconstructed images in a computer readable storage medium. In one embodiment, the reconstructor 216 stores reconstructed images in the system memory 320 of the computing device 316. In another embodiment, the reconstructor 216 stores reconstructed images in a remote or cloud-based computer readable storage medium. Furthermore, image reconstructor 216 may transmit reconstructed images to the computing device 316 for generating useful patient information for diagnosis and evaluation. In certain embodiments, the computing device 316 may transmit the reconstructed images and/or the patient information to a display that is connected to the computing device 316.

In one embodiment, image reconstructor 216 may include computer readable program instructions, and may apply the methods described herein to reconstruct an image. In another embodiment, the system memory 320 may include the computer readable program instructions stored in and may apply the methods described herein, at least in part, to a reconstructed image after receiving the reconstructed image from image reconstructor 216. In yet another embodiment, methods and processes described herein may be distributed across image reconstructor 216 and computing device 316.

The computing device 316 is further connected to and is in communication with the IAPS 102. When connected to the computing device 316, IAPS 102 may be specifically adapted to a single imaging modality (i.e., a CT imaging system).

Figure 4:
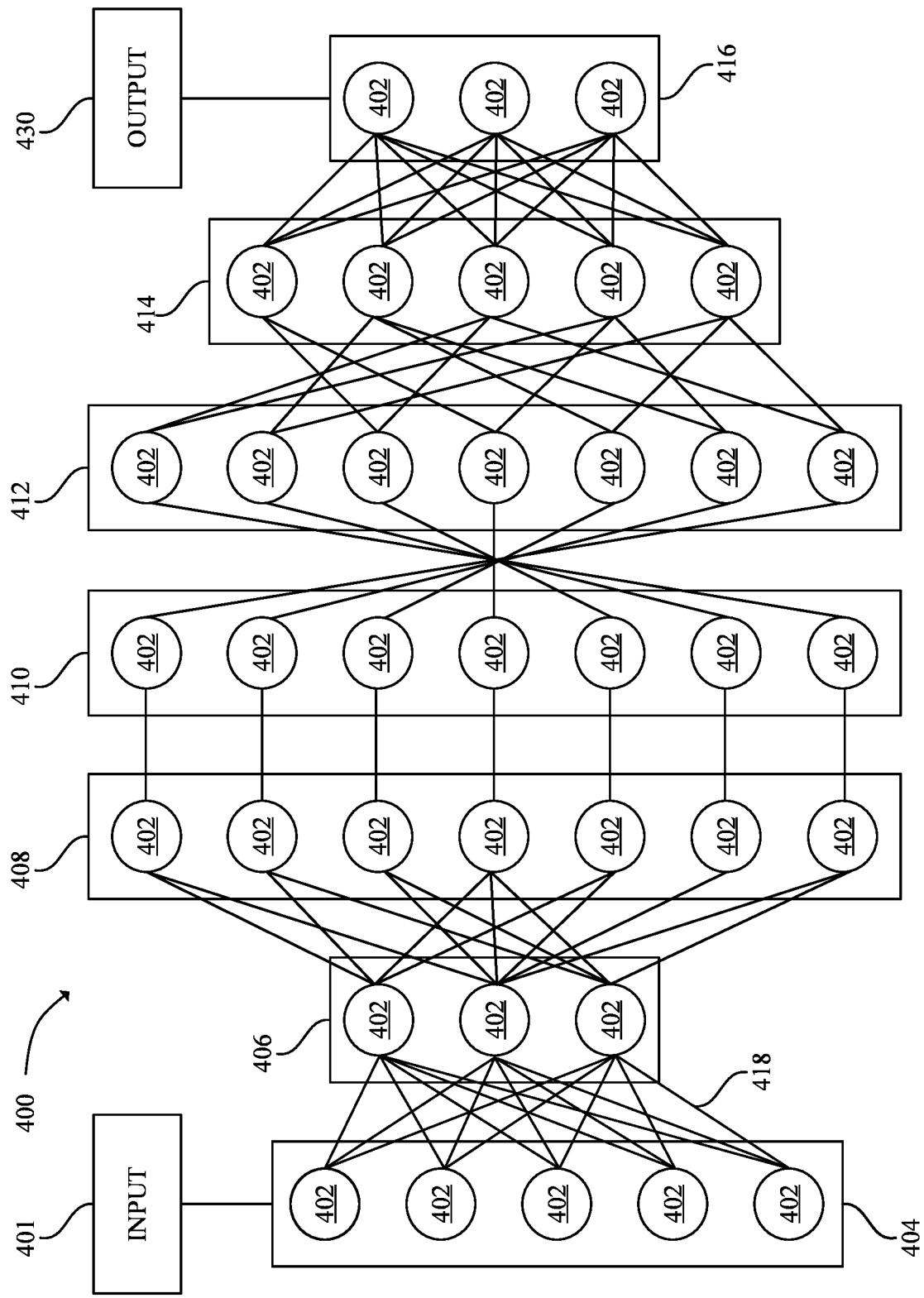
FIG. 4 is a schematic diagram of a neural network in accordance with an exemplary embodiment.

Referring now to FIG. 4, a neural network 400 is shown in accordance with an exemplary embodiment. The neural network 400 may be a deep neural network and may be implemented by the IAPS 102. The neural network 400 includes a plurality of neurons (or nodes) 402 which are disposed across layers 404, 406, 408, 410, 412, 414, and 416. As used herein with respect to neurons, the term "layer" refers to a collection of simulated neurons that have inputs and/or outputs connected in similar fashion to other collections of simulated neurons. Accordingly, as show in FIG. 4, neurons 402 may be connected to each other via one or more connections 418 such that data may propagate from an input layer 404, through one or more intermediate layers 406, 408, 410, 412, and 414, to an output layer 416.

Figure 5:
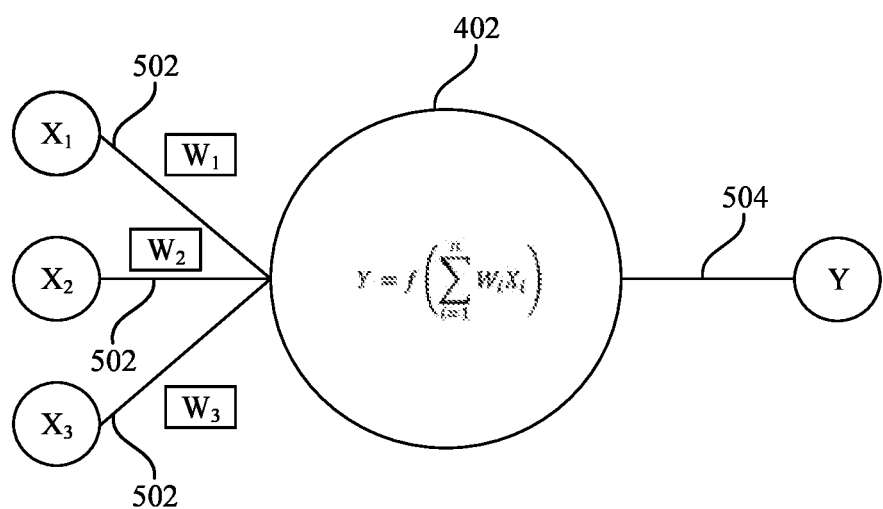
FIG. 5 is a schematic diagram of a neuron of a neural network in accordance with an exemplary embodiment.

Referring now to FIG. 5, an input/output connection between neurons of a neural network is shown in accordance with an exemplary embodiment. As shown in FIG. 5, connections (i.e., connections 418) of an individual neuron 402 may include one or more input connections 502 and one or more output connections 504. Each input connection 502 of neuron 402 may be an output connection of a preceding neuron 402, and each output connection 504 of neuron 402 may be an input connection of one or more subsequent neurons. While FIG. 5 depicts neuron 402 as having a single output connection 504, it should be understood that neurons may have multiple output connections that send/transmit/pass the same value. In some embodiments, neurons 402 may be data constructs (i.e., structures, instantiated class objects, matrices, etc.) and input connections 502 may be received by neuron 402 as weighted numerical values (i.e., floating point or integer values). For example, as further shown in FIG. 5, input connections $X_1$, $X_2$, and $X_3$ may be weighted by weights $W_1$, $W_2$, and $W_3$, respectively, summed, and sent/transmitted/passed as output connection Y. As will be appreciated, the processing of an individual neuron 402 may be represented generally by the equation:

$$Y = f\left(\sum_{i=1}^{n} W_i X_i\right)$$

where n is the total number of input connections 502 to neuron 402. In one embodiment, the value of Y may be based at least in part on whether the summation of $W_iX_i$ exceeds a threshold. For example, Y may have a value of zero (0) if the summation of the weighted inputs fails to exceed a desired threshold.

As will be further understood from FIGS. 4 and 5, input connections 502 of neurons 402 in input layer 404 may be mapped to an input 401, while output connections 504 of neurons 402 in output layer 416 may be mapped to an output 430. As used herein, "mapping" a given input connection 502 to input 401 refers to the manner by which input 401 affects/dictates the value said input connection 502. Similarly, as also used herein, "mapping" a given output connection 504 to output 430 refers to the manner by which the value of said output connection 504 affects/dictates output 430.

Accordingly, in some embodiments, the acquired/obtained input 401 is passed/fed to input layer 404 of neural network 400 and propagated through layers 404, 406, 408, 410, 412, 414, and 416 such that mapped output connections 504 of output layer 416 generate/correspond to output 430. Input 401 may include medical imaging protocols retrieved from the master global protocol library 110, medical imaging protocols generated by the IAPS 102, a queried medical imaging procedure from the user device 106 (or another computing device), and/or further medical data related to the queried medical imaging procedure from the IT systems 108. As will be discussed in further detail herein, each of the medical imaging protocols and the queried medical imaging procedure may include protocol tags identified and generated by the neural network 400 as output 430. After identification and generation, the protocol tags may be matched to attribute values in ontological identifiers (i.e., RadLex® Playbook identifiers), as described in detail below with reference to FIG. 10 For example, the neural network 400 may identify one or more imaging modalities, modality modifiers, body regions (i.e., anatomical regions), and pharmaceutical indicators for each scanner level protocol and queried medical imaging procedure.

Neural network 400 may be trained over time against accumulated protocol selections, where the accumulated protocol selections may be based on received medical information (i.e., patient clinical information, a reason for a corresponding exam order, etc.). In some embodiments, the neural network 400 may improve consistency by receiving incremental updates to a local mapping library in the form of medical imaging protocol selections mapped to grouped medical imaging protocols. The incremental updates may include automated selections of scanner level protocols selected by the IAPS 102 and confirmed by the medical professional and/or manual selections of scanner level protocols from the medical professional. In some embodiments, the incremental updates may further include the received medical information, such as orders, clinical indications, and patient medical history (i.e., patient allergies, prior exams, prior reports, etc.). It will be appreciated that, in some examples, the neural network 400 may not be employed to identify protocol tags until a threshold number of manual selections of scanner level protocols have been received. In this way, the neural network 400 may adaptively learn to identify and protocol tags (i.e., outputs) from received scanner level protocols or queried medical imaging procedures (i.e., inputs). The machine learning, or deep learning, therein (due to, for example, identifiable trends in scanner level protocol selection at a given medical facility) may cause weights (i.e., $W_1$, $W_2$, and/or $W_3$) to change, input/output connections to change, or other adjustments to neural network 400. Further, as additional medical expertise is accumulated (i.e., by way of received protocol selections), the machine learning may continue to adjust various parameters of the neural network 400 in response. As such, a sensitivity of the neural network 400 may be periodically increased, resulting in a greater consistency, which ultimately may improve a consistency in automated medical imaging protocol selection.

Figure 6:
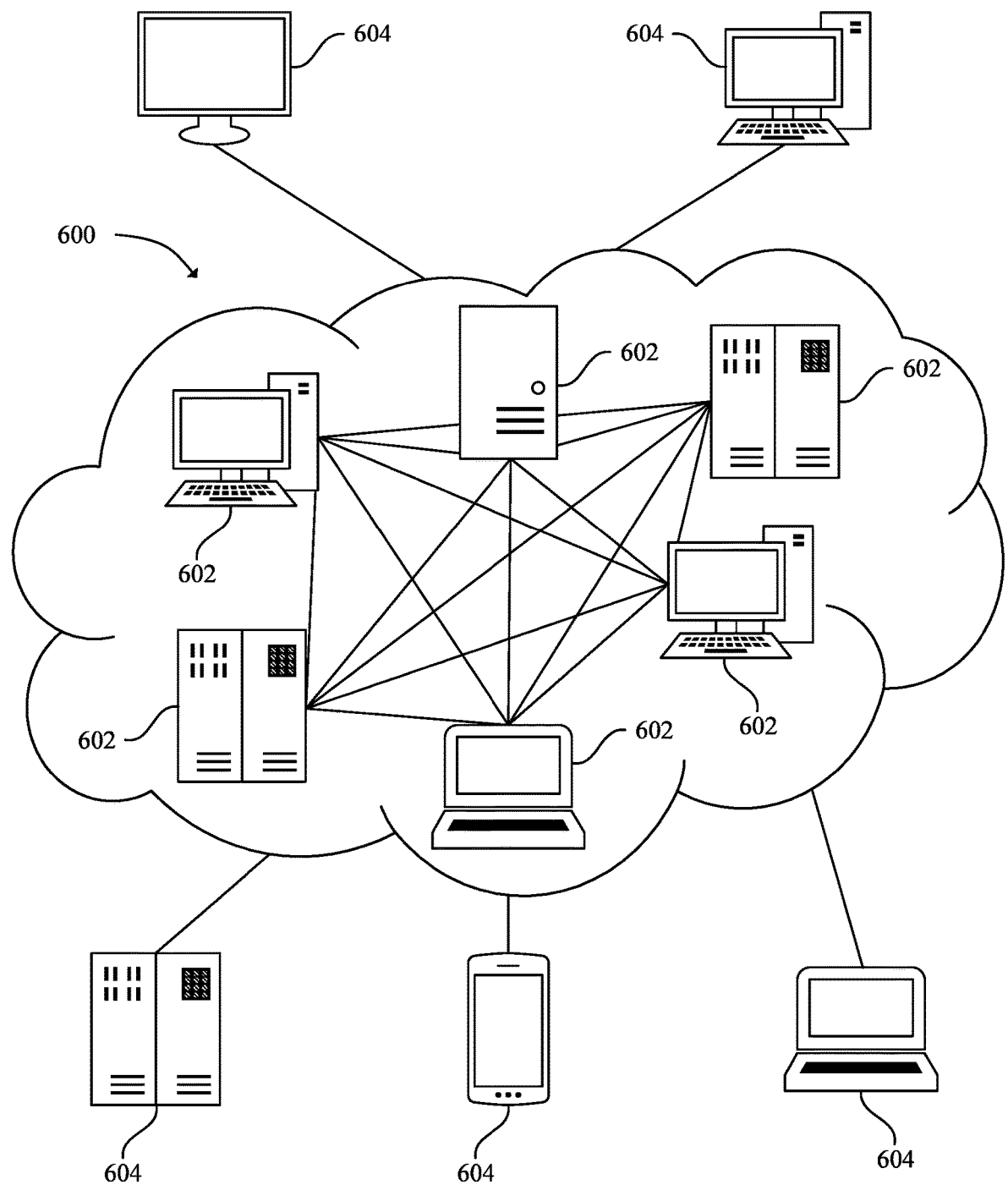
FIG. 6 depicts a cloud computing environment in accordance with an exemplary embodiment.

Referring now to FIG. 6, a cloud computing environment 600 is shown in accordance with an exemplary embodiment. As illustrated in FIG. 6, in some embodiments, the cloud computing environment 600 includes one or more nodes 602. Each node 602 may include a computer system/server (i.e., a personal computer system, a server computer system, a mainframe computer system, etc.). In some embodiments, one or more nodes 602 may include the IAPS 102, the IT systems 108, the global protocol library 110, the reconstructor 216, the PACS 324 and/or a local protocol library including the local mapping library 322. The nodes may communicate with one another and may be grouped into one or more networks. Each node 602 may include a computer readable storage medium and a processor that executes instructions in the computer readable storage medium. As further illustrated in FIG. 6 one or more devices (or systems) 604 may be connected to the cloud computing environment 600. The one or more devices 604 may be connected to a same or different network (i.e., LAN, WAN, public network, etc.). The one or more devices 604 may include components of the medical imaging system 100, the CT system 200, and the CT system 300. One or more nodes 602 may communicate with the devices 604 thereby allowing the computing devices 602 to provide software services to the devices 604.

Figure 7:
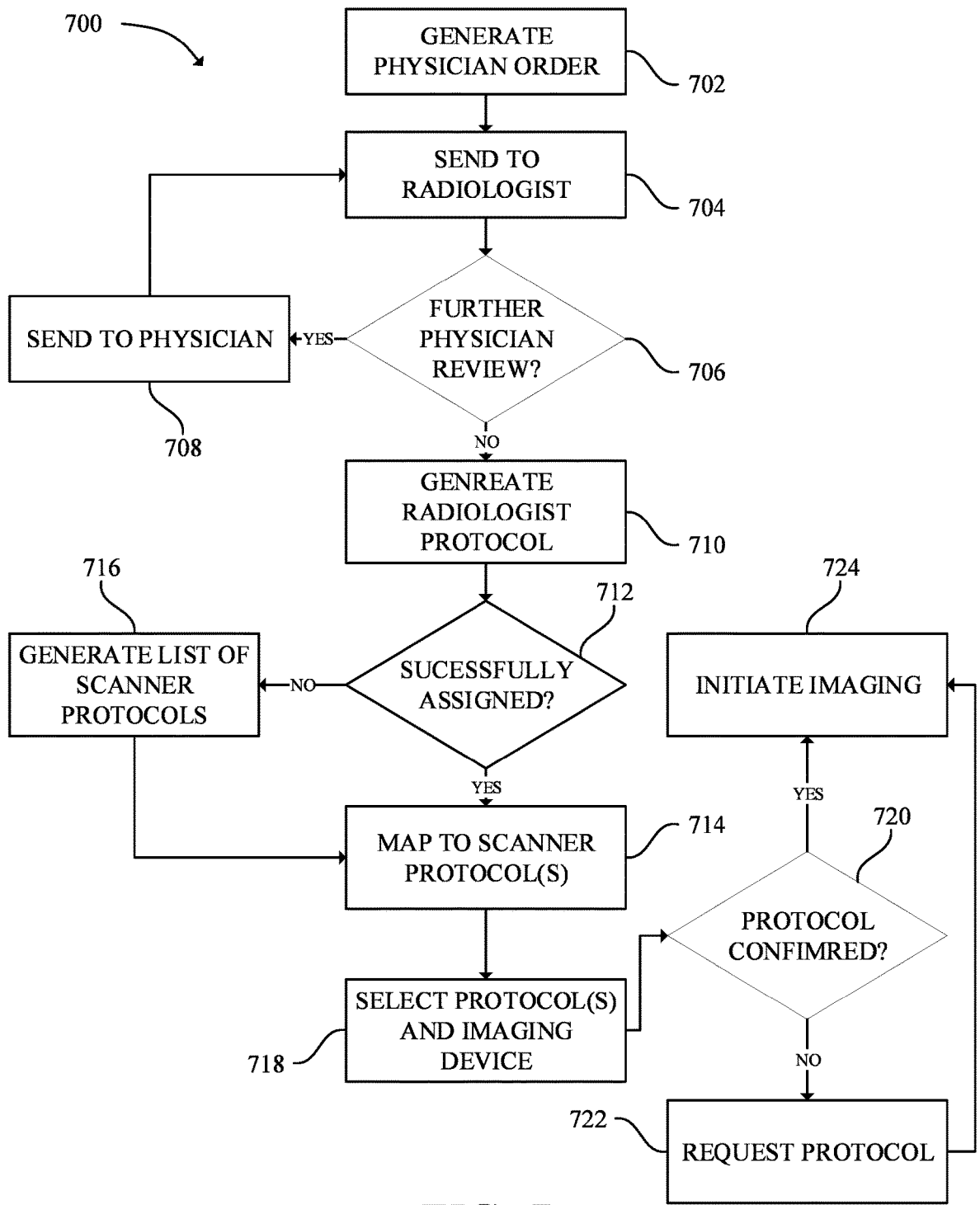
FIG. 7 is a flow chart of a method for automating the selection of medical imaging protocols in accordance with an exemplary embodiment.

Referring now to FIG. 7, a flow chart of a method 700 for automating the selection of medical imaging protocols is shown in accordance with an exemplary embodiment. Various aspects of the method 700, 800, 900, 1000, 1100, and 1200 depicted in FIGS. 7-12 may be carried out by a "configured processor." As used herein, a configured processor is a processor that is configured according to an aspect of the present disclosure. A configured processor(s) may be the processor 112, the processor 130, a processor of a node 602, or a processor of a device 604. A configured processor executes various computer readable program instructions to perform the steps of the methods 700, 800, 900, 1000, 1100, and 1200. In one embodiment, the IAPP 116 includes the instructions to perform the steps of the methods 700, 800, 900, 1000, 1100, and 1200. The computer readable program instructions, that when executed by a configured processor, cause a configured processor to carry out the steps of the methods 700, 800, 900, 1000, 1100, and 1200 are stored in a computer readable storage medium including, but not limited to, the system memory 114, the system memory 132, a system memory of a node 602, or a system memory of a device 604. The technical effect of the methods 700, 800, 900, 1000, 1100, and 1200 is automating the selection of medical imaging protocols.

The method 700 may be implemented in numerous medical settings. For example, since multiple steps in the method 700 may be performed by one or more medical professionals, the method 700 may be implemented at a relatively large medical facility having sufficient medical professionals to perform such steps. It will be appreciated, however, that other medical settings may be contemplated within the scope of the present disclosure At 702, the configured processor generates physician order for a patient to be imaged. In one embodiment, the configured processor generates the physician order as a function of a selected physician order that is provided to a physician. In this embodiment, the configured processor may output a list of physician orders to a GUI of a display. The displayed physician orders may include an imaging modality (i.e., CT, MRI, PET, etc.) and a region to be imaged (i.e., head, leg, abdomen, foot, etc.). The physician may enter patient identifying information into a computer device (i.e., the user device 106, a device 604, etc.) of an HIS via one or more external devices (i.e., mouse, keyboard etc.) to access a corresponding EMR. The physician may review medical information stored in the EMR to determine which of the physician orders in the displayed list is necessary. In one example, the physician may review a patient EMR that includes information relating to abdominal pain. In this example, the physician may determine a CT scan of the abdomen is necessary to properly diagnose the cause of the pain. As such, the physician may select "CT scan, abdomen" from the list of displayed physician orders. In another example, the physician may review a patient EMR that includes information relating to a brain tumor. In this example, the physician may determine an MRI of the head is necessary to diagnose the stage of the brain tumor. As such, the physician may select "MM, head" from the list of displayed physician orders. In another embodiment, the physician may select more than one physician order. In this embodiment, the configured processor generates a physician order that includes orders for multiple imaging procedures.

In another embodiment, the configured processor may generate a physician order as a function of text entered into a physician order form displayed in a GUI via an external device. In this embodiment, the physician may access, and review information stored in an EMR and enter text corresponding to a physician order into the physician order form. For example, the physician may review information in an EMR and determine a CT coronary angiogram is needed. Accordingly, the physician may enter "CT coronary angiogram" in the physician order form which causes the configured processor to generate a physician order that includes "CT coronary angiogram." In another embodiment, the physician may enter text corresponding to more than one medical imaging procedure. For example, the physician may enter "CT scan of the abdomen with contrast and CT scan of the abdomen without contrast" into the physician order form. In this embodiment, the configured processor generates a physician order that includes orders for multiple medical imaging procedures.

At 704, the configured processor sends the physician order and a prompt asking if further physician review is needed to a radiologist device. The radiologist device may be the user device 106 or a device 604. In some examples, the physician may be located at a remote location, such as at a clinician's office. In other examples, the physician may be in a separate department of a medical facility relative to the radiologist. In response to receiving the physician order, a radiologist reviews the physician order. In some examples, the first medical professional may be located at a remote location, such as at a clinician's office.

At 706, the configured processor determines if the physician needs to further review the physician order. The configured processor determines whether further review is needed as a function of a received selected to a prompt. In some embodiments, the radiologist device may be a computing device with a display. In these embodiments, the display may show the prompt and physician order. In response to receiving the physician order, the radiologist may review the physician order and medical information stored in an EMR to determine whether further review from the physician is desired. In one example, the radiologist may receive a physician order for John Doe that includes a CT scan of the head. After reviewing medical information in John Doe's EMR, the radiologist may determine John Doe should have a CT scan of the abdomen rather than a CT scan of the head as John Doe is experiencing abdominal pain. Accordingly, the radiologist may select "yes" to the prompt asking if further physician review is needed as John Doe may need to undergo a CT scan of the abdomen rather than a CT scan of the head. In response to the radiologist selecting "yes," the configured processor determines further physician review is needed.

In another example, the radiologist may receive a physician order for Jane Doe that includes an MRI of the abdomen. After reviewing medical information in Jane Doe's EMR, the radiologist may determine Jane Doe should have an MM of the head as Jane Doe may have a brain tumor. Accordingly, the radiologist may select "no" to the prompt asking if further physician review is needed as Jane Doe the radiologist determined the physician order indicates the correct medical imaging procedure. In response to the radiologist selecting "no," the configured processor determines further physician review is not needed.

At 708, in response to determining the physician needs to further review the physician order, the configured processor sends the physician order to a physician device. In some embodiments, the physician device may be a computing device with a display. In these embodiments, the configured processor may output the physician order and a notification indicating further review is needed to the physician device. In response to receiving the physician order, the physician may review physician order to confirm and/or update the physician order.

At 710, in response to determining the physician does not need to further review the physician order, the configured processor generates a radiologist level protocol and, in some embodiments, outputs the generated radiologist level protocol to a display. A radiologist level protocol may include an imaging modality, a region to be imaged, an imaging order/direction, and a patient position. The configured processor generates the radiologist level protocol as a function of the physician order, medical information relating to the patient to be imaged stored in an IT system including the IT systems 108, previously selected radiologist level protocols, previously generated radiologist level protocols, and medical imaging protocols stored in a global protocol library including the global protocol library 110. In one embodiment, the processor 112 of the IAPS is the configured processor and generates the radiologist level protocol.

In one example, a physician order for John Doe may include a CT scan of the head without contrast. In this example, the EMR for John Doe may indicate John Doe is 10 years old, 4' 6" tall, and weights 70 lbs. As such, the configured processor may generate a radiologist level protocol that includes a routine CT helical brain scan for a child without contrast. In another example, a physician order for Jane Doe may be for a knee ultrasound. In this example, a radiologist level protocol may include a knee ultrasound with a linear transducer wherein the sagittal supine leg is bet with anterior drawn movement.

In one embodiment, the configured processor may generate a plurality of radiologist level protocols and may output the plurality of radiologist level protocols in a list. In this embodiment, each of the radiologist level protocols may be assigned a confidence weight (i.e., based on a degree of a similarity to the physician order), such that a radiologist level protocol having a highest weight may be output first in the list. In some embodiments, each radiologist level protocol having a weight higher than a threshold weight may be output.

At 712, the configured processor determines if the radiologist level protocol may be successfully assigned to a scanner level protocol and written to an IT system 108 (i.e., RIS 122). The configured processor determines if the radiologist level protocol may be assigned to a scanner level protocol as a function previously mapped radiologist protocols to scanner level protocols stored in a local mapping library (i.e., the local mapping library 322). For example, a radiologist protocol generated at 710 may include information that is the same as a previously generated radiologist level protocol. In this example, a local mapping library indicates the previously generated radiologist level protocol was successfully mapped to a given scanner level protocol. In this example, the configured processor determines the radiologist level protocol generated at 710 may be mapped to the same scanner level protocol as the previously generated radiologist level protocol as both the radiologist level protocol generated at 710 and the previously generated radiologist protocol includes the same information.

At 714, in response to determining the radiologist level protocol may successfully assigned to a scanner level protocol, then the configured processor maps the radiologist level protocol to a scanner level protocol. The scanner level protocols may be stored in the global protocol library 110. In one embodiment, the configured processor may determine the radiologist level protocol may be successfully assigned to a group of scanner level protocols. In this embodiment, the radiologist level protocol may be mapped to grouped scanner level protocols (i.e., other, substantially similar scanner level protocols). A scanner level protocol may include a region to be imaged, a scan order, and a setting pertaining to a specific medical imaging device.

At 716, in response to determining the radiologist level protocol may not be assigned to a scanner level protocol, then the configured processor generates a prioritized list of scanner level protocols along with a notification indicating that a radiologist or a technologist must further format the scanner level protocols to a given medical imaging device format.

At 718, the configured processor selects a scanner level protocol and a medical imaging device 104. In one embodiment, wherein the configured processor mapped the radiologist level protocol to only one scanner level protocol, the configured processor selects that scanner level protocol. In another embodiment, wherein the configured processor mapped the radiologist level protocol to a group of scanner level protocols, the scanner level protocols may be assigned a confidence weight (i.e., based on a degree of a similarity to the radiologist level protocol) and the configured processor may select the scanner level protocols with a score above a given threshold. For example, the configured processor may have mapped the radiologist level protocol to three scanner level protocols including a first scanner level protocol, a second scanner level protocol, and a third scanner level protocol. In this example, the first scanner level protocol may have a higher confidence weight than the second or third scanner level protocols as the first scanner protocol is more similar to the second or third scanner level protocols. For example, the first scanner protocol may include settings pertaining to a CT scan of the abdomen with contrast whereas the second and third scanner level protocols include settings pertaining to a CT scan of the abdomen without contrast. Accordingly, the first scanner level protocol is the most similar to a radiologist level protocol relating to a CT scan of the abdomen with contrast.

Furthermore, the configured processor may interface with a plurality of medical imaging devices 104, wherein each medical imaging device 104 corresponds to a different imaging modality and the selected scanner level protocol is specific to a given imaging modality and imaging device 104. Accordingly, scanner level protocol may therefore be assigned to the imaging device 104 corresponding to a given imaging modality and thus the selected imaging device 104 is configured to execute the selected scanner level protocol.

At 720, the configured processor outputs the selected scanner level protocol(s) to a GUI and determines if a technologist has confirmed a scanner level protocol for imaging. When the selected scanner level protocols include a plurality of scanner level protocols, the configured processor outputs the selected scanner level protocols in a list wherein the highest scored selected scanner level protocol appears first. In one embodiment, the configured processor determines the technologist has confirmed the scanner level protocol as a function of a user input. For example, the when the configured processor outputs one or more scanner level protocols to a GUI, the technologist may utilize an external device to select a scanner level protocol. In response to the selection, the configured processor determines the technologist has confirmed the scanner level protocol for imaging. The configured processor may determine that a technologist has not confirmed a scanner level protocol as a function of a user input. For example, the GUI may include an icon that states "protocol missing" or the like. In response to the technologist selecting this icon, the configured processor determines the technologist has not confirmed a scanner level protocol.

At 722, in response to determining that the technologist has not confirmed a scanner level protocol, the configured processor outputs a prompt requesting a scanner level protocol to the GUI and receives a manually entered scanner level protocol. The prompt may include a list of scanner level protocols that were not previously output the GUI. The technologist may utilize an external device to select a scanner level protocol.

At 724, in response to determining the technologist has confirmed a scanner level protocol or in response to a user supplying a protocol, the configured processor initiates an imaging procedure at the selected medical imaging device 104 based on confirmed scanner level protocol. Specifically, configured processor may translate the confirmed scanner level protocol to a scanner level protocol executable, which may then be executed by the medical imaging as the scan medical imaging procedure.

Each of the scanner level protocols and the medical imaging device 104 may either be automatically selected by the configured process and confirmed by the technologist, or one or both of the scanner level protocol and the medical imaging device 104 may instead be manually confirmed/selected by the technologist. Regardless of how the confirmation/selection is made, a local mapping library may then be updated. The local mapping library may include information as to mapping of the assigned radiologist level protocol to the grouped scanner level protocols (i.e., at 712), as well as mapping of the automatically confirmed scanner level protocol to the scanner level protocol actually executed to initiate the scan session. In this way, a consistency of scanner level protocol selection may be incrementally improved over time by updating the local protocol library with each scanner level protocol confirmation.

Figure 8:
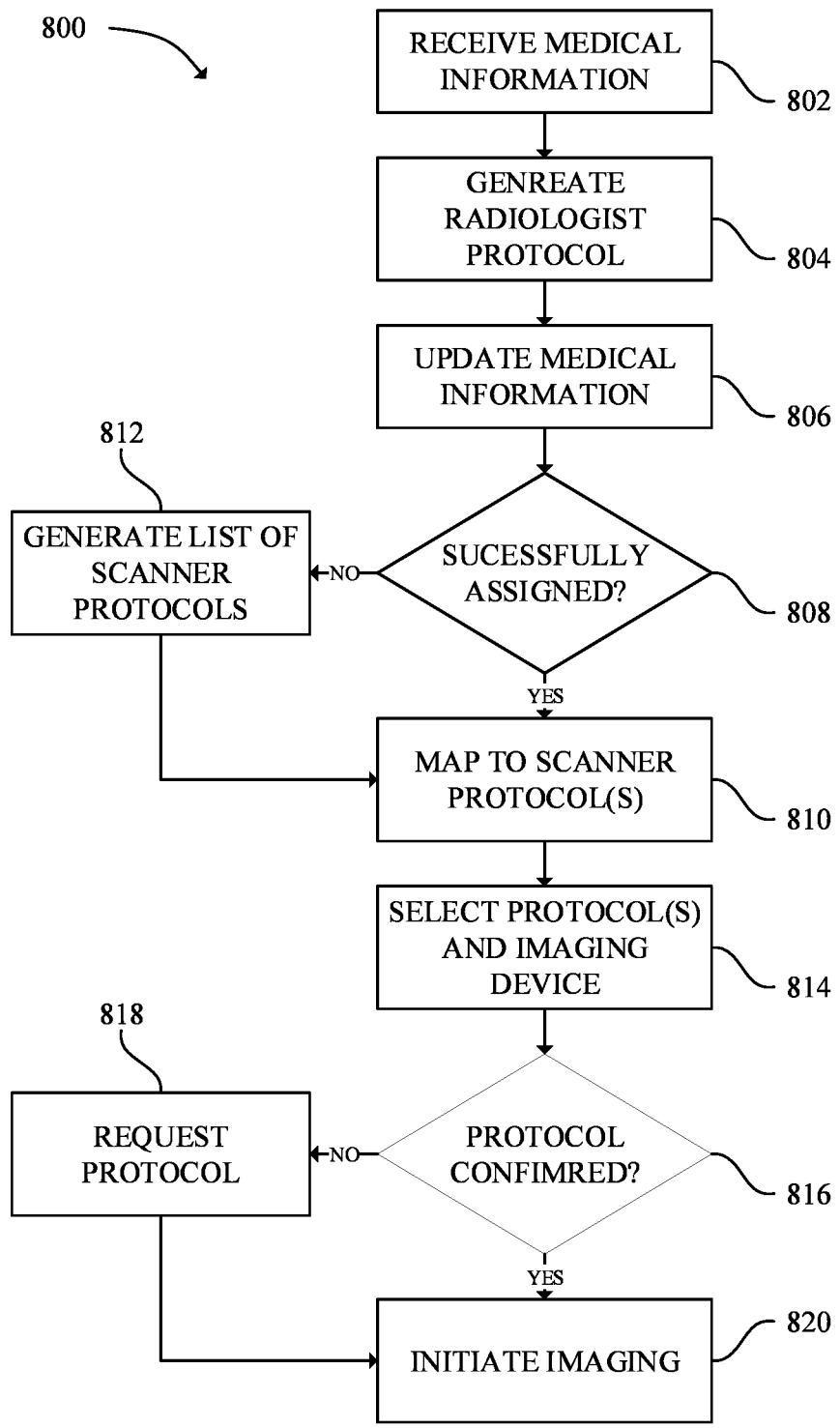
FIG. 8 is a flow chart of another method for automating the selection of medical imaging protocols in accordance with an exemplary embodiment.

Referring now to FIG. 8, another flow chart of a method 800 for automating the selection of medical imaging protocols is shown in accordance with an exemplary embodiment.

The method 800 may be implemented in numerous medical settings. The method 800 may be implemented at a relatively small medical facility having insufficient medical professionals to perform such steps efficiently. It will be appreciated, however, that other medical settings may be contemplated within the scope of the present disclosure.

At 802, the configured processor receives medical information for a patient to be imaged. In one embodiment, the configured processor the configured processor receives the medical information as a function of medical information entered into a computing device by a medical professional (i.e., physician, radiologist, technician, etc.). In another embodiment, the configured processor receives the medical information from one or more of the IT systems 108. The medical information may include, but is not limited to, a physician order, clinical indications, and medical history for a given patient. For example, the configured processor may receive a physician order selected by a physician from the EMR/HIS 120 corresponding to an electronic medical record for a given patient. The physician may enter clinical indications and medical history from the EMR/HIS to a GUI displayed by the display 134 of the user device or another computing device. The received medical information may further include prior exam images and prior reports from one or more of the IT systems 108 based on a received physician order. For example, medical professional may retrieve prior exam images from the PACS 124 and prior reports from the RIS 122, the prior reports and prior exam images correspond to the patient to be imaged or to other patients with similar medical issues as the patient to be imaged.

At 804, the configured processor generates a radiologist level protocol. The configured processor generates the radiologist level protocol as a function of the received medical information as well as medical information collected from prior radiologist level protocol generation and confirmation/selection stored in a local mapping library. Each of the one or more radiologist level protocols may be assigned a confidence weight (i.e., based on a degree of a similarity to the order), such that the configured processor outputs a radiologist level protocol having a highest weight to a display of a computing device. In some embodiments, each radiologist level protocol having a weight higher than a threshold weight may output. It will therefore be appreciated that the method 800 may generate and output one or more radiologist level protocols.

At 806, the configured processor may then update the received medical information and store the updated medical information on (i.e., write the medical data back to) one or more IT systems 108. As an example, the configured processor may update an EMR for the patient to be imaged indicating the generated/output radiologist level protocol. As another example, the configured processor system may be configured to output an additional report to the RIS based on the generated radiologist level protocol for use with future protocol generation.

It will be appreciated that 808-820 the method 800 may be respectively described in a substantially similar manner to 712-724 of the first exemplary method 700 as described above with reference to FIG. 7. As such, further description of remaining steps of the method 800 are omitted for brevity, and reference is made to corresponding steps of the method 700 with reference to FIG. 7.

Methods 900, 1000, 1100, and 1200 of FIGS. 9-12 show exemplary embodiments for selecting scanner level protocols with a semantic search algorithm. The methods 900, 1000, 1100, and 12000 may be implemented at steps 712-724 of method 700 and steps 808-820 of method 800 wherein scanner level protocols are selected. The semantic search algorithm is stored on a computer readable storage medium and may be executed by a processor. In one embodiment, the IAPP 116 may include the semantic search algorithm. The neural network 400 may be configured to identify and extract domain concepts from a queried medical imaging procedure. A queried medical imaging procedure may be within a medical imaging protocol (i.e., physician order, radiologist level protocols, etc.) or other medical imaging order. While, methods 900, 1000, 1100, and 1200 are described below with regard to the systems and components depicted in FIGS. 1-3. However, it will be appreciated that the methods 900, 1000, 1100, and 1200 may be implemented with other systems and components without departing from the scope of the present disclosure In some embodiments, the exemplary neural network 400 may identify protocol tags (i.e., corresponding to domain concepts) from the scanner level protocols received from a global protocol library. The exemplary neural network may similarly identify and protocol tags from a medical imaging query such that the protocol tags from the medical imaging query may ultimately be matched to protocol tags from at least some of the scanner level protocols. A medical imaging query includes a query for a scanner level protocol relating to a medical imaging procedure (i.e., a medical imaging procedure defined in a physician or radiologist level protocol). Accordingly, in some embodiments, the method 900 may be applied at steps 712-718 to match a radiologist level protocol to one or more scanner level protocols. Once the medical imaging query is matched to one or more scanner level protocols (and therefore a medical imaging protocol with the query is matched to one or more scanner level protocols), a configured processor may select the matched scanner level protocols for output to a display. Thereafter, a scanner level protocol may be automatically confirmed or confirmed by a technologist and translated to an executable for initiating an imaging procedure at a medical imaging device, such as via method 1200 with reference to FIG. 12.

Figure 9:
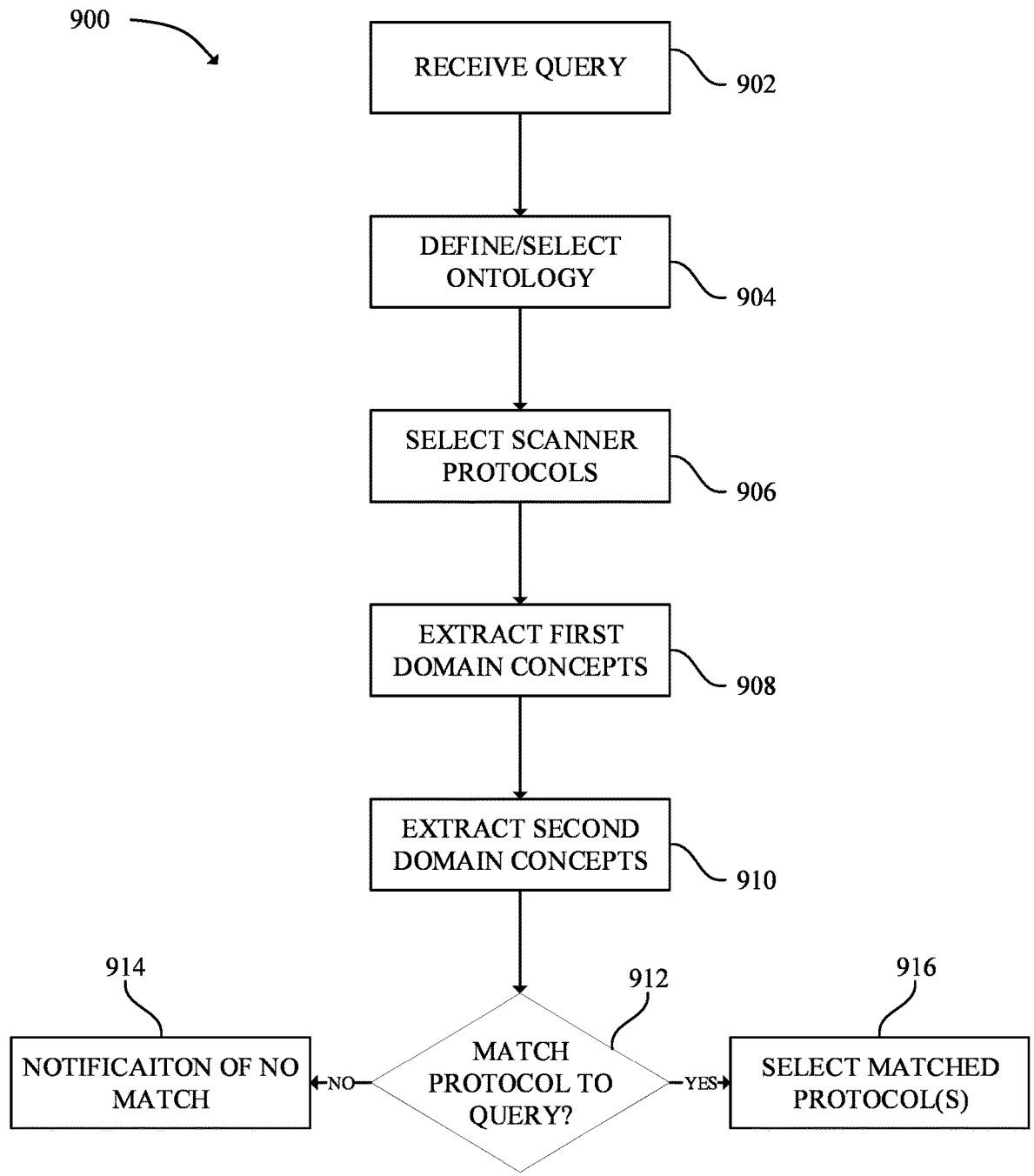
FIG. 9 is a flow chart of a method for selecting scanner level protocols with a semantic search algorithm in accordance with an exemplary embodiment.

Referring now to FIG. 9, a flow chart of a method 900 for selecting scanner level protocols with a semantic search algorithm is shown in accordance with an exemplary embodiment. Specifically, the steps of method 900 include receiving a medical imaging query and matching a scanner level protocol to the received query. In some embodiments, the medical imaging query may be within a medical imaging protocol including, but not limited to, a radiologist level protocol generated at step 710 of method 700.

At 902, the configured processor receives a medical imaging query. In some embodiments the configured processor may be automatically supplied the medical imaging query after a radiologist level protocol with the medical imaging query is generated at 710 or 804. In other embodiments, a user may provide the medical query to the configured processor via an input device (i.e., keyboard, mouse, etc.) communicably coupled a computing device (i.e., the user device 106). The query is then received by the semantic search algorithm. In additional or alternative embodiments, the query may include other associated medical information, such as clinical indications, medical histories, prior exam images, prior reports, etc. Such medical information may be useful in determining personalized protocol selections for specific patients (i.e., different scanner level protocols may be selected based on patient size, patient allergies, patient preexisting conditions, etc.).

At 904, the configured processor may define or select an ontology. The configured processor may define or select an ontology as a function of information in the received medical imaging query. In general, the defined or selected ontology may include a standardized set of identifiers keyed to domain concepts, and relationships between the identifiers. For example, the ontology may be the RadLex® radiology lexicon relating the medical imaging query and the identifiers may be RadLex® Playbook identifiers (RPIDs) that relate to medical imaging query.

At 906, the configured processor selects a plurality of scanner level protocols from a global protocol library. The configured processor may select the plurality of scanner level protocols as a function of information in the received medical imaging query. The plurality of scanner level protocols may include all scanner level protocols stored in a global protocol library, or a subset thereof. For example, if the medical imaging query includes information relating to a CT scan, the configured processor may select scanner level protocols relating to CT scans.

At 908, the configured processor extracts a plurality of first domain concepts from the scanner level protocols. Specifically, the semantic search algorithm may first match the scanner level selected from the global protocol library at 906 to identifiers in the ontology defined or selected at 904. Then the matched identifiers may be mapped to identifiers matched to prior protocol selections, such that the plurality of first domain concepts may be identified and extracted based on a mapping stored in a local mapping library. For example, each identifier may correspond to a subset of domain concepts, such that, once an identifier in a known (i.e., defined or selected) ontology is determined, the subset of domain concepts may be determined based on the identifier. Further details regarding matching of the identifiers with the scanner level protocols and extracting the plurality of first domain concepts therefrom are described below with reference to FIG. 10.

Figure 10:
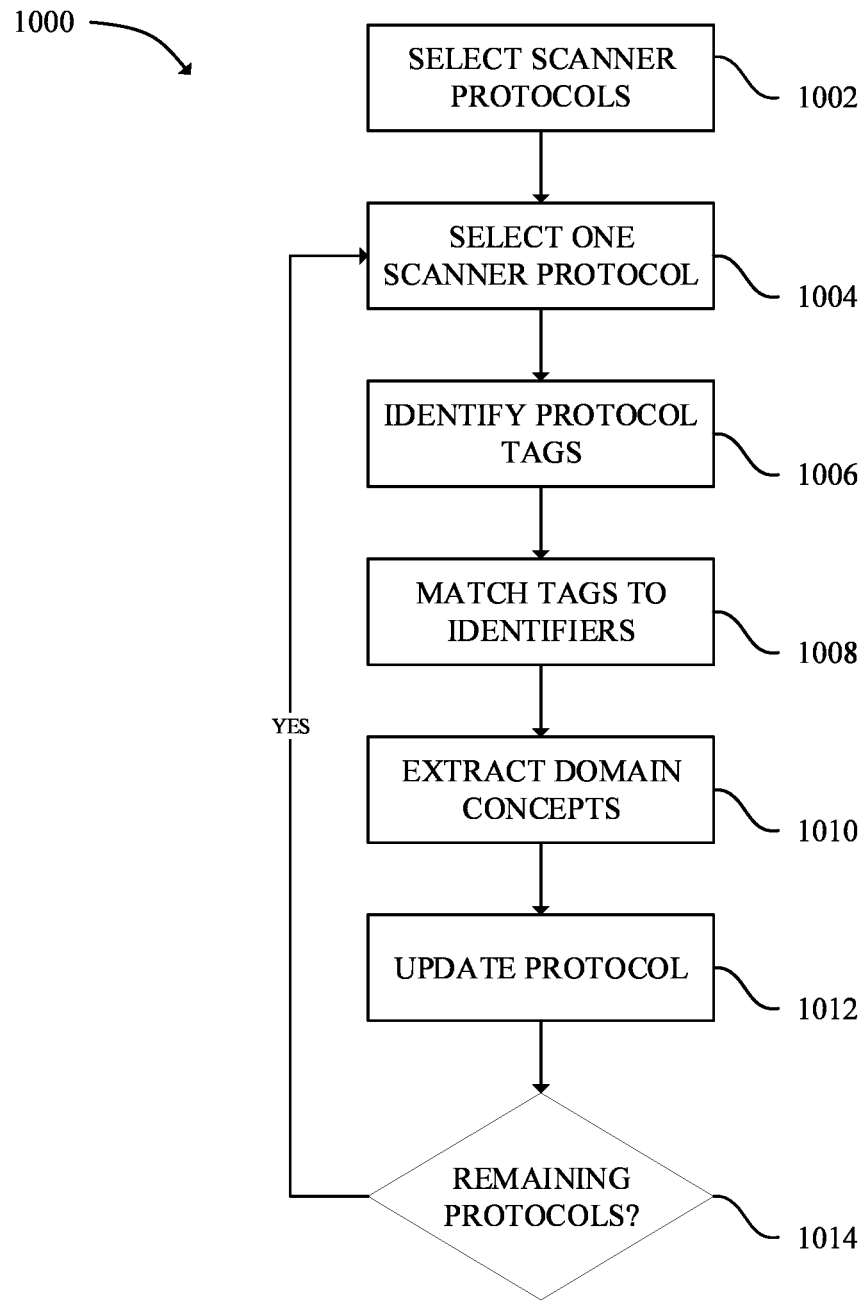
FIG. 10 is a flow chart of a method for matching a plurality of scanner level protocols to identifiers from an exemplary ontology in accordance with an exemplary embodiment.

Referring now to FIG. 10, a flow chart of a method 1000 for matching a plurality of scanner level protocols to identifiers from an exemplary ontology is shown in accordance with an exemplary embodiment. Specifically, the plurality of scanner level protocols may be assigned to a plurality of identifiers such that corresponding domain concepts may be identified and extracted from each scanner level protocol. It will be appreciated that a substantially similar method for matching a queried medical imaging procedure with the identifiers is within the scope of the present disclosure and is not described more explicitly for brevity. However, one of at least ordinary skill in the art would be able to readily adapt aspects of method 1000 to matching the queried medical imaging procedure to the identifiers. As such, it will be appreciated that, in some embodiments, method 1000 may be implemented within method 900.

At 1002, the configured processor selects a plurality of scanner level protocols from a global protocol library. The configured processor may select the plurality of scanner level protocols as a function of information in the received medical imaging query. The plurality of scanner level protocols may include all scanner level protocols stored in the global protocol library, or a subset thereof.

At 1004, the configured processor selects a scanner level protocol from the plurality of scanner level protocols. It will be appreciated that, though 1004 to 1010 are directed to sequential tagging of each scanner level protocol of the plurality of scanner level protocols, 1004 to 1010 may be executed simultaneously within the scope of the present disclosure.

At 1006, the configured processor identifies a plurality of protocol tags for the selected protocol. In some embodiments, the selected protocol may be input into a neural network (i.e., the neural network 400 of FIGS. 4 and 5) implementing semantic search paradigms. In such embodiments, the neural network may output the plurality of protocol tags based on prior protocol tag identification. The plurality of protocol tags may uniquely identify a plurality of attribute values corresponding to an imaging modality, a plurality of body regions (i.e., three body regions), a modality modifier, and a pharmaceutical indicator. For example, the imaging modality may be "CT," the plurality of body regions may be "abdomen," "pelvis," and "lower extremity," the modality modifier may be "angiography," and the pharmaceutical indicator may be "with an intravenous tube.

At 1008, the configured processor matches the plurality of protocol tags to one or more identifiers in an ontology. In some embodiments, the ontology may be the RadLex® radiology lexicon and the identifiers may be RPIDs. The semantic search algorithm may determine an exact match between the plurality of protocol tags and a given RPID. In some examples, at least some of the plurality of protocol tags may be remapped. For example, the pharmaceutical indicator may be remapped to "with" or "without." Any protocol tag not specified may be considered as blank for the purposes of matching to the one or more identifiers.

At 1010, the configured processor extracts a plurality of domain concepts based on the one or more identifiers. For example, detailed information and attribute values may be keyed to each of the one or more identifiers and retrieved from an ontological database (i.e., the RadLex® Playbook).

At 1012, the configured processor updates the selected scanner level protocol with the one or more identifiers and the plurality of extracted domain concepts. In this way, the identifiers and extracted domain concepts of the scanner level protocols may be leveraged to determine matches therebetween, or between a given scanner level protocol and a queried medical imaging procedure.

At 1014, the configured processor determines whether a last scanner level protocol in the plurality of scanner level protocols has been selected. If there are scanner level protocols in the plurality of scanner level protocols which have not yet been selected, method 1000 may return to 1002. However, if each scanner level protocol in the plurality of scanner level protocols has been selected, method 1000 may end.

Returning now to FIG. 9 at 910, the configured processor extracts a plurality of second domain concepts from the queried medical imaging procedure. After matching the scanner level protocols selected from a global protocol library to the identifiers in the ontology, the semantic search algorithm may then match the queried medical imaging procedure to the identifiers in the ontology in a similar fashion. The identifiers matched to the queried medical imaging procedure may then be mapped to identifiers matched to prior protocol selections, such that the plurality of second domain concepts may be identified and extracted based on the mapping. The prior protocol selections may be stored in a local mapping library. It will be appreciated that matching the identifiers with the queried medical imaging procedure and extracting the plurality of second domain concepts therefrom may be performed via a method substantially similar to the method described above with reference to FIG. 10 for matching the identifiers to the scanner level protocols and extracting the plurality of first domain concepts therefrom. As such, further details of extracting the plurality of second domain concepts from the queried medical imaging procedure are omitted for brevity but remain within the scope of the present disclosure.

At 912, the configured processor determines whether a match between any of the plurality of scanner level protocols and the query (i.e., the queried medical imaging procedure) exists based on the pluralities of first and second domain concepts. It will be appreciated that 912 to 916 are described broadly, and that a more specific embodiment therefor is described below with reference to FIG. 11. However, it will further be appreciated that other matching and selection steps may be contemplated without departing from the scope of the present disclosure.

At 914, in response to failing to determine a match (i.e., if there is no overlap or too little overlap between the plurality of first and second domain concepts, the similarities between the semantics of a given first domain concept and a given second domain do not exceed a threshold, etc.), the configured processor a notification that no protocol selections were made by the semantic search algorithm. The notification may include text indicating that no match was determined, and, in some embodiments, the configured processor may output the notification to a display.

At 916, in response to determining one or more matches (i.e., if overlap between the plurality of first and second domain concepts, the similarities between the semantics of a given first domain concept and a given second domain do exceed a threshold, etc.), the configured processor selects each scanner level protocol corresponding to the one or more matches and outputs the selected scanner level protocols to a display. In one embodiment, each of the one or more selected scanner level protocols may be assigned a confidence weight based on a degree of overlap of the match to the queried medical imaging procedure. In this embodiment, the selected scanner level protocols may be output to a display in a list wherein the scanner level protocol with the highest confidence weight is listed first. In another embodiment, wherein each of the one or more selected scanner level protocols is assigned a confidence weight based on a degree of overlap of the match to the queried medical imaging procedure, the configured processor may output only the scanner level protocols with a confidence weight greater than a threshold.

Figure 11:
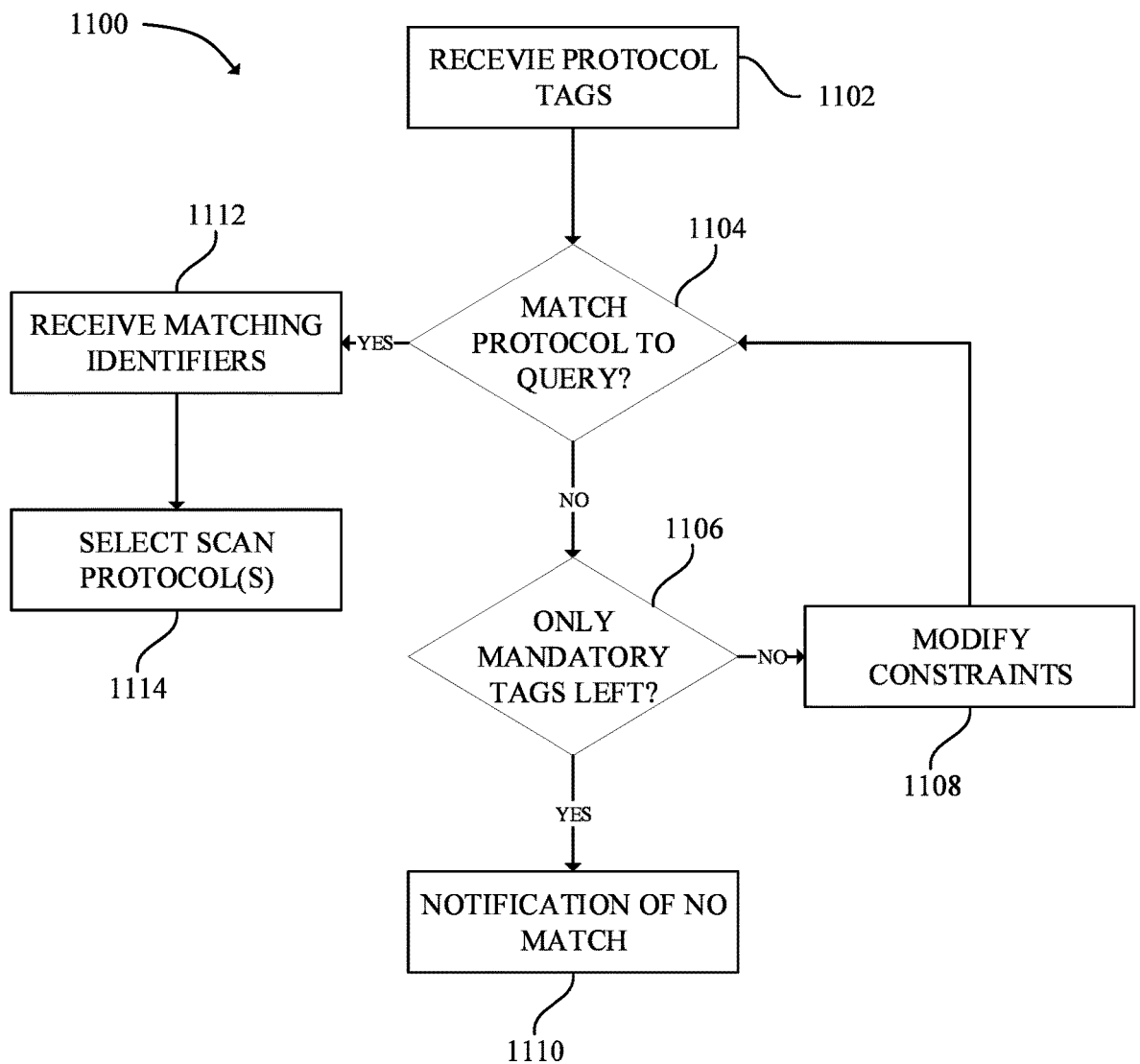
FIG. 11 is flow chart of a method for matching a plurality of scanner level protocols to a queried medical imaging procedure in accordance with an exemplary embodiment.

Referring now to FIG. 11, a flow chart of a method 1100 for matching a plurality of scanner level protocols to a queried medical imaging procedure is shown in accordance with an exemplary embodiment. Specifically, since each scanner level protocol of a plurality of scanner level protocols and the queried medical imaging procedure may be associated with respective identifiers from an exemplary ontology, method 1100 may include determining matching identifiers between the plurality of scanner level protocols and the queried medical imaging procedure within one or more matching constraints.

At 1102, the configured processor receives a plurality of first protocol tags and a first identifier for each scanner level protocol of a plurality of scanner level protocols and a plurality of second protocol tags and a second identifier for a queried medical. Prior to receipt at 1102, the queried medical imaging procedure and each scanner level protocol may have been matched to a corresponding plurality of protocol tags and identifier by a semantic search algorithm. In some embodiments, each identifier may be an RPID from the RadLex® radiology lexicon. In such embodiments, the plurality of protocol tags may uniquely identify a plurality of attribute values, wherein the plurality of attribute values is associated with the identifier for the corresponding scanner level protocol. It will be appreciated that, with reference to method 900, each of the first identifiers and the pluralities of first protocol tags may correspond to the plurality of first domain concepts, and the each of the second identifier and the plurality of second protocol tags may correspond to the plurality of second domain concepts.

At 1104, the configured processor determines whether a match between any of the plurality of scanner level protocols and the queried medical imaging procedure exists based on the first and second identifiers. In some embodiments, the match may be an exact alphanumeric match between the identifiers. In additional or alternative embodiments, the match may be determined responsive to a plurality of matching constraints being met. The plurality of matching constraints may include the plurality of first protocol tags matching the plurality of second protocol tags, or a subset of the plurality of first protocol tags matching a corresponding subset of the plurality of second protocol tags. For example, each of the subsets may include protocol tags corresponding to the same attributes (i.e., imaging modality, body regions, modality modifier, pharmaceutical indicator, etc.).

At 1106, in response to determining no matches, the configured processor determines whether only mandatory protocol tags are left in the subsets of first and second protocol tags corresponding to the plurality of matching constraints. Specifically, mandatory protocol tags may include a minimum number of specified protocol tags which may correspond to the plurality of matching constraints. For example, the mandatory protocol tags may include those protocol tags corresponding to the imaging modality, at least one of the body regions, and the pharmaceutical indicator.

At 1108, in response to determining there are more protocol tags other than the mandatory protocol tags left in the subsets of first and second protocol tags corresponding to the plurality of matching constraints at 1106, the configured processor modifies the plurality of matching constraints. Specifically, modifying the plurality of matching constraints may include reducing the subsets of first and second protocol tags by one or more protocol tags. For example, if the subsets of first and second protocol tags correspond to the imaging modality, the body regions, the modality modifier, and the pharmaceutical indicator, then the modality modifier may be removed from the subsets of first and second protocol tags in an attempt to determine whether a match between any of the plurality of scanner level protocols and the queried medical imaging procedure exists based on the first and second identifiers.

At 1110, in response to determining only mandatory protocol tags are left in the subsets of first and second protocol tags corresponding to the plurality of matching constraints, the configured processor generates a notification that no protocol selections were made by the semantic search algorithm. Specifically, the notification may be generated when no matches between any of the plurality of scanner level protocols and the queried medical imaging procedure were determined by the semantic search algorithm, even upon modifying the plurality of matching constraints until only mandatory protocol tags remained in the subsets of first and second protocol tags. In some embodiments, the notification includes text and the configured processor outputs the notification to a display.

At 1112, in response to determining one or more matches, the configured processor correspondingly receives one or more matching identifiers.

At 1114, the configured processor selects each scanner level protocol respectively corresponding to the one or more matching identifiers and outputs the selected scanner level protocols to a display.

Figure 12:
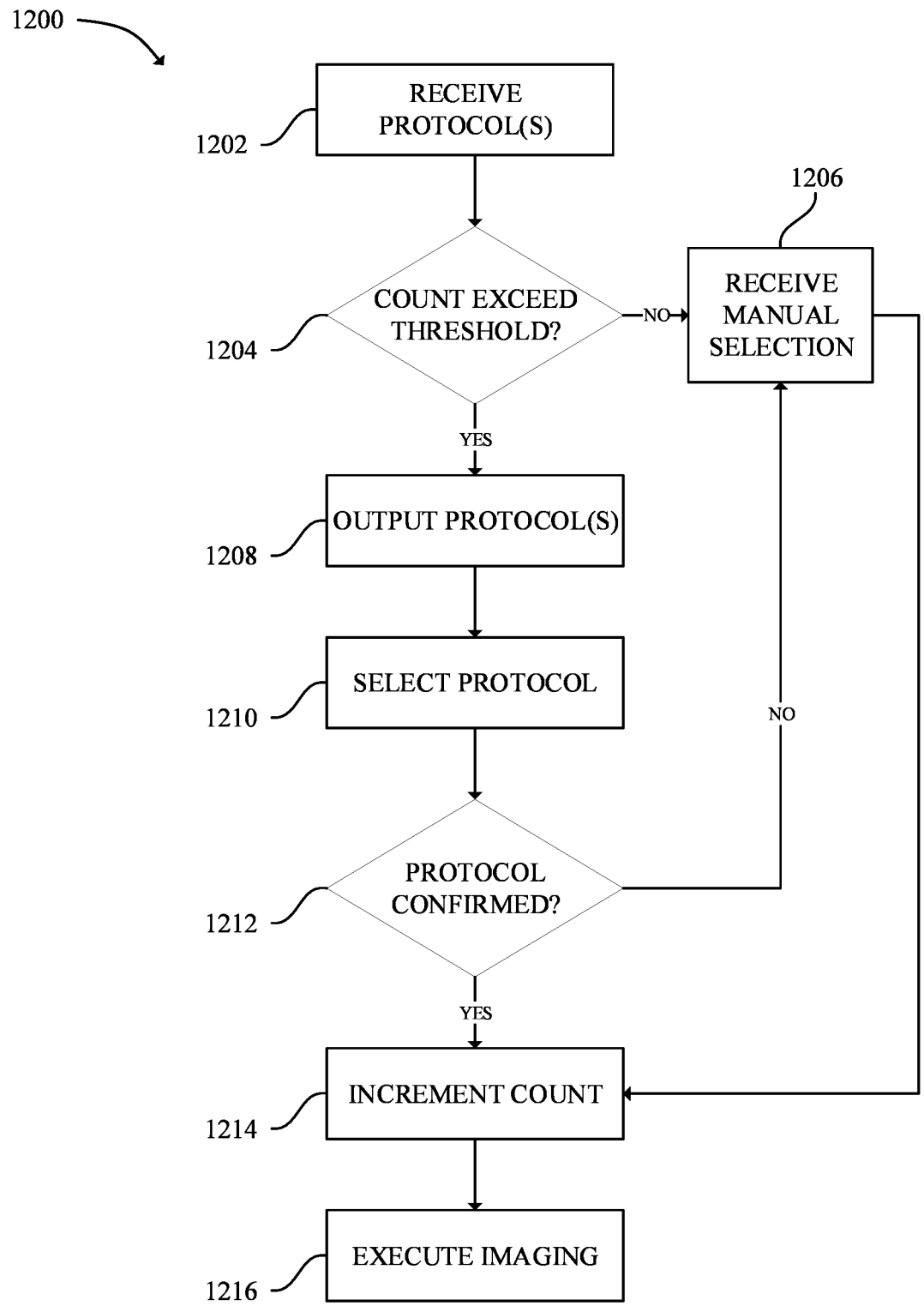
FIG. 12 is a flow chart of a method for selecting a scanner level protocol from one or more scanner level protocols.

Referring now to FIG. 12, a flow chart of a method 1200 for selecting a scanner level protocol from one or more scanner level protocols (i.e., scanner level protocols previously selected by the semantic search algorithm) and executing a scan session based on the selected scanner level protocol is shown in accordance with an exemplary embodiment. Specifically, selecting of the scanner level protocol may depend at least in part upon previous selections made, either automatically by the configured processor or by a medical professional (i.e., a technologist). Following selection of the scanner level protocol, the medical imaging procedure corresponding to the selected scanner level protocol may be executed.

Method 1200 is described below with regard to the systems and components depicted in FIGS. 1-3. However, it will be appreciated that method 1200 may be implemented with other systems and components without departing from the scope of the present disclosure. In some embodiments, method 1200 may be implemented as computer readable program instructions stored in a computer readable storage medium.

At 1202, the configured processor receives one or more scanner level protocols. In one embodiment, the scanner level protocols include the scanner level protocols selected at 916 of method 900.

At 1204, the configured processor determines whether a selection count of at least of the received scanner level protocols is greater than a threshold selection count. In some embodiments, the selection count of a given scanner level protocol may be a total number of instances in which a scanner level protocol was selected and implemented in a medical imaging procedure over a predetermined duration, or since the IAPS 102 was actuated. In other embodiments, the selection count of the scanner level protocol may be an average selection count, wherein the average selection count may be determined by a linear weighted moving average (LWMA). Specifically, the LWMA may be based on confidence weights associated with the at least one protocol selection, where the confidence weights may be based on segments of selection counts over the predetermined duration. In one embodiment, each of the segments may include 20 selection counts and the predetermined duration may be 12 months. In additional or alternative embodiments, the selection counts may be specific to a patient or to a subset of similar patients, such that the configured processor may generate personalized protocol selections.

At 1206, in response to determining no selection count of any of the received scanner level protocols exceeds the threshold, the configured processor receives a manual selection of the scanner level protocol from a user of the medical imaging system. That is, since none of the selection counts of the one or more received scanner level protocols exceeded the threshold selection count, no scanner level protocols are displayed to the user, and the manual selection may be provided as an alternative. In some embodiments, however, in response to determining no selection count of any of the received scanner level protocols exceeds the threshold, the configured processor generates and outputs a notification to a display. The notification informs the user that no selection count of any of the received scanner level protocols exceeded the threshold.

At 1208, in response to determining at least one section count of a received scanner level protocol exceeds the threshold, the configured processor outputs the at least one scanner level protocol to a display. In this way, the configured processor may be less likely to output scanner level protocols inconsistent with previously selected scanner level protocols (whether automatically, i.e., by the configured processor, or, i.e., by the user of medical imaging system).

In some embodiments, the at least one scanner level protocols may be displayed as a sorted list. As an example, the sorted list may be sorted by selection count, such that a protocol selection having a highest selection count may be displayed at a top of the sorted list. As an example, the sorted list may be sorted by confidence weight, such that a scanner level protocol having a highest confidence weight may be displayed at the top of the sorted list. In additional or alternative embodiments, only a maximum number of protocol selections may be displayed. For example, up to six protocol selections of the at least one protocol selections (i.e., protocol selections having highest confidence weights of the at least one protocol selections) may be displayed at the display device At 1210, the configured processor selects one of the scanner level protocols with a selection count that exceeds the threshold including but not limited one of the scanner level protocols output to a display at 1208. In one embodiment, the configured processor selects the protocol having the highest confidence weight.

At 1212, the configured processor determines whether confirmation of the selected protocol is received. In some embodiments, the confirmation may be received from the user of the medical imaging system. However, in other embodiments, the confirmation may be made by a subroutine (i.e., a virtual assistant). In some embodiments, if the level of confidence of a given protocol selection is below a threshold level of confidence, then confirmation may be sought from a medical professional with a relatively high experience level (i.e., a radiologist). Conversely, if the level of confidence of the given protocol selection is above the threshold level of confidence, then confirmation may be sought from a medical professional with a relatively low experience level (i.e., a technologist), from the subroutine, or from a combination thereof. In some embodiments, automatic selection from the at least one protocol selections may be actuatable by the user of the medical imaging system, such that, in individual instances, automatic selection may not be utilized.

At 1214, in response to determining confirmation of the selected protocol selection is not received, the configured processor receives the manual selection of the scanner level protocol from the user of a medical imaging system at 1206. In some embodiments, the manual selection may include a user selection of one of the at least one protocol selections displayed to the user. In additional or alternative embodiments, the manual selection may include a user selection of a scanner level protocol not corresponding to any of the at least one protocol selections displayed to the user.

At 1216, in response to determining the confirmation was received, (i.e., at 1212), or if the manual selection is received (i.e., at 1206), the configured processor increment a selection count (i.e., by one) of a selected scanner level protocol. As such, the selected scanner level protocol may correspond to the confirmed, automatically selected protocol selection or to a manually selected scanner level protocol.

At 1218, the configured processor executes a medical imaging procedure based on the selected scanner level protocol. Specifically, the configured processor may translate the selected scanner level protocol to a scanner level protocol executable, which may then be executed by a scanner of the medical imaging system as the medical imaging procedure.

In this way, an intelligent automated protocoling system for a medical imaging system is provided for initiating scan sessions based on automatically selected scanner level protocols. Specifically, in some examples, the intelligent automated protocoling system may select and execute a scanner level protocol specific to a given patient and medical issue responsive to confirmation of the scanner level protocol from a medical professional. In other examples, however, the medical professional may fail to provide confirmation, and may instead manually provide an alternate scanner level protocol. In either case, for each scan session, the intelligent automated protocoling system may immediately update a local mapping library based on input from the medical professional. A technical effect of updating the local mapping library based on such incremental feedback from one or more medical professionals is that the intelligent automated protocoling system may alter protocol selections over time for a given medical situation based on accumulated medical expertise gleaned from the incremental feedback. In some examples, the intelligent automated protocoling system may further be configured to select a scanner specific to the selected scanner level protocol. A technical effect of automated scanner selection is that an appropriate medical imaging modality to a given medical situation may be consistently determined based on the accumulated medical expertise, thereby improving patient experience and health outcomes.

As discussed herein, the intelligent automated protocoling system may supplant and improve upon previous steps performed manually by various medical professionals. It will be appreciated that the complex interrelation of data structures assessed and synthesized by the intelligent automated protocoling system may not be accomplished manually (i.e., by a medical professional) with a comparable degree of fidelity. Specifically, the intelligent automated protocoling system of the present disclosure may improve upon a consistency in scanner level protocol selection by asynchronously updating a local mapping library relative to IT systems storing raw medical data utilized for such scanner level protocol selection. In this way, a concomitant consistency in medical treatment across profession, geography, and imaging modality may be achieved, thereby improving patient experience and health outcomes.

In addition to any previously indicated modification, numerous other variations and alternative arrangements may be devised by those skilled in the art without departing from the spirt and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments are meant to be illustrative only and should not be construed to be limiting in any manner.

What is claimed is:

1. A method comprising:
  receiving an order for an imaging procedure, wherein the imaging procedure corresponds to a patient;
  in response to receiving the order, obtaining medical information stored in an information technology system, wherein the medical information relates to the patient;
  automatically generating an imaging protocol as a function of the received order and the obtained medical information;
  translating the generated imaging protocol to a scan protocol executable, the generated imaging protocol comprising a region of the patient to be imaged, an imaging order/direction, a patient position, or a combination thereof, wherein the generated imaging protocol is identified, using a neural network, from a query comprising one or more protocol tags;
  initiating an imaging procedure specific to the patient based on the scan protocol executable; and
  executing the scan protocol executable by a scanner of a medical imaging system to generate a medical image, wherein executing the scan protocol executable comprises generating the medical image based on one or more technical imaging parameters for the medical imaging system.

2. The method of claim 1, wherein the imaging protocol is a radiologist level imaging protocol.

3. The method of claim 1, further comprising:
  updating the medical information and storing the updated medical information on the information technology system.

4. The method of claim 1, wherein the information technology system stores an electronic medical record that corresponds to the patient and the medical information is within the electronic medical record.

5. The method of claim 1, wherein the information technology system further includes a radiological information system that stores at least one previously generated report that corresponds to the patient and the medical information is within the at least one previously generated report that corresponds to the patient.

6. The method of claim 1, further comprising:
  mapping a scanner level imaging protocol to a radiologist level imaging protocol as a function of previous scanner level imaging protocol selections.

7. A method comprising:
  receiving a plurality of scan protocols and a plurality of patient-specific medical information from one or more storage devices;
  extracting a plurality of first domain concepts from the plurality of scan protocols and a plurality of second domain concepts from the plurality of patient-specific medical information; and
  in response to matching a subset of the plurality of scan protocols to the plurality of patient-specific medical information based on the plurality of first domain concepts and the plurality of second domain concepts:
  selecting of one scan protocols in the subset of scan protocols;
  translating the selected scan protocol to a scan protocol executable, the selected scan protocol comprising a region of a patient to be imaged, an imaging order/direction, a patient position, or a combination thereof, wherein the selected scan protocol is identified, using a neural network, from a query comprising one or more protocol tags;
  initiating an imaging procedure specific to the patient based on the scan protocol executable; and
  executing the scan protocol executable by a scanner of a medical imaging system to generate a medical image, wherein executing the scan protocol executable comprises generating the medical image based on one or more technical imaging parameters for the medical imaging system.

8. The method of claim 7, wherein the plurality of first domain concepts and the plurality of second domain concepts are extracted based on a local mapping library.

9. The method of claim 8, further comprising:
updating the local mapping library based on the selection.

10. The method of claim 9, further comprising:
in response to no subset of the plurality of scan protocols being matched to the plurality of patient-specific medical information:
receiving a manual selection of one of the plurality of scan protocols, and
updating the local mapping library based on the manual selection.

11. The method of claim 8, wherein in the local mapping library is asynchronously updated with respect to the one or more storage devices.

12. The method of claim 7, wherein the plurality of patient-specific medical information comprises a queried imaging procedure and one or more of clinical indications, medical history, prior exam images, and prior reports from a radiological information system.

13. The method of claim 7, wherein the plurality of first domain concepts and the plurality of second domain concepts are extracted via the neural network.

14. The method of claim 13, wherein extracting the plurality of first domain concepts and the plurality of second domain concepts comprises:
generating and identifying, via the neural network, a plurality of first protocol tags for the plurality of scan protocols and a plurality of second protocol tags for the plurality of patient-specific medical information;
extracting the plurality of first domain concepts based on the plurality of first protocol tags; and
extracting the plurality of second domain concepts based on the plurality of second protocol tags.

15. A computer readable storage medium with computer readable program instructions that, when executed by a processor, cause the processor to:
receive a plurality of scan protocols and a plurality of patient-specific medical information from one or more storage devices;
extract a plurality of first domain concepts from the plurality of scan protocols and a plurality of second domain concepts from the plurality of patient-specific medical information;
in response to matching a subset of the plurality of scan protocols to the plurality of patient-specific medical information based on the plurality of first domain concepts and the plurality of second domain concepts;
select one of the scan protocols in the subset of scan protocols;
translate the selected scan protocol to a scan protocol executable, the selected scan protocol comprising a region of a patient to be imaged, an imaging order/direction, a patient position, or a combination thereof, wherein the selected scan protocol is identified, using a neural network, from a query comprising one or more protocol tags;
initiate an imaging procedure specific to the patient based on the scan protocol executable; and
execute the scan protocol executable by a scanner of a medical imaging system to generate a medical image, wherein executing the scan protocol executable comprises generating the medical image based on one or more technical imaging parameters for the medical imaging system, wherein the one or more technical imaging parameters comprise a contrast parameter, a timing parameter, a scan speed parameter, an anatomic coverage parameter, or a combination thereof.

16. The computer readable storage medium of claim 15, wherein the computer readable program instructions, when executed by the processor, further cause the processor to:
initiate an imaging procedure based on the selected scan protocol.

17. The computer readable storage medium of claim 15, wherein the plurality of first domain concepts and the plurality of second domain concepts are extracted based on a local mapping library.

18. The computer readable storage medium of claim 17, wherein the computer readable program instructions, when executed by the processor, further cause the processor to:
asynchronously update the local mapping library with respect to the one or more storage devices.

19. The method of claim 1, wherein the one or more technical imaging parameters comprise a contrast parameter, a timing parameter, a scan speed parameter, an anatomic coverage parameter, or a combination thereof.

* * * * *